(12) United States Patent
Sakamoto et al.

(10) Patent No.: US 10,182,569 B2
(45) Date of Patent: Jan. 22, 2019

(54) COMPOSITION COMPRISING ALLANTOIN AND METHOD OF APPLYING ALLANTOIN TO A PLANT

(71) Applicant: Kaneka Corporation, Osaka (JP)

(72) Inventors: Atsushi Sakamoto, Hiroshima (JP); Hiroshi Shimada, Hiroshima (JP); Shoma Tanaka, Hiroshima (JP); Masutoshi Nojiri, Hyogo (JP); Yu Fu, Hyogo (JP); Noriyuki Kizaki, Hyogo (JP); Mitsuaki Kitano, Hyogo (JP)

(73) Assignee: KANEKA CORPORATION, Osaka (JP)

(*) Notice: Subject to any disclaimer, the term of this patent is extended or adjusted under 35 U.S.C. 154(b) by 0 days.

(21) Appl. No.: 15/977,890

(22) Filed: May 11, 2018

(65) Prior Publication Data
US 2018/0279619 A1    Oct. 4, 2018

Related U.S. Application Data

(63) Continuation-in-part of application No. PCT/JP2017/032452, filed on Sep. 8, 2017, and a
(Continued)

(30) Foreign Application Priority Data

Jan. 29, 2016 (JP) .................................. 2016-016383
Mar. 7, 2016 (JP) .................................. 2016-043503
Sep. 8, 2016 (JP) .................................. 2016-175752

(51) Int. Cl.
*A01N 47/36*    (2006.01)
*A01N 25/02*    (2006.01)
(Continued)

(52) U.S. Cl.
CPC ............... *A01N 47/36* (2013.01); *A01G 7/00* (2013.01); *A01G 9/24* (2013.01); *A01G 20/00* (2018.02);
(Continued)

(58) Field of Classification Search
CPC .......... A01G 7/00; A01G 20/00; A01G 22/22; A01G 9/24; A01N 25/02; A01N 47/36
See application file for complete search history.

(56) References Cited

U.S. PATENT DOCUMENTS 6,221,370 B1    4/2001 Wadle et al.
2006/0005281 A1    1/2006 Shinozaki et al.
(Continued)

FOREIGN PATENT DOCUMENTS

CN    102603432 A    7/2012
CN    104137846 A    11/2014
(Continued)

OTHER PUBLICATIONS

Valentine, R, "Mechanism of the Allantoin Fermentation", Jul. 1962, The Journal of Biological Chemistry, vol. 237, No. 7, pp. 2271-2277. (Year: 1962).*
(Continued)

*Primary Examiner* — Michael H Wang
(74) *Attorney, Agent, or Firm* — Osha Liang LLP

(57) ABSTRACT

A method for cultivating a plant includes applying allantoin to a plant; exposing the plant to a temperature of about 30° C. or more for at least about 60 minutes; and growing the plant in a cultivation medium.

20 Claims, 12 Drawing Sheets

Specification includes a Sequence Listing.

US 10,182,569 B2
Page 2

Related U.S. Application Data continuation-in-part of application No. PCT/JP2016/089061, filed on Dec. 28, 2016.

(51) Int. Cl.
| | |
|---|---|
| *A01G 7/00* | (2006.01) |
| *A01G 22/22* | (2018.01) |
| *C05G 3/00* | (2006.01) |
| *A01G 9/24* | (2006.01) |
| *A01G 20/00* | (2018.01) |

(52) U.S. Cl.
CPC ............ *A01G 22/22* (2018.02); *A01N 25/02* (2013.01); *C05G 3/00* (2013.01)

(56) References Cited

U.S. PATENT DOCUMENTS

| | | | |
|---|---|---|---|
| 2007/0173459 A1 | 7/2007 | Filippini | |
| 2010/0333237 A1* | 12/2010 | Fluhr | A01N 3/00 800/298 |
| 2011/0030099 A1* | 2/2011 | Ryals | C12N 15/8218 800/285 |
| 2015/0128304 A1 | 5/2015 | Shinozaki et al. | |
| 2015/0181884 A1 | 7/2015 | Fluhr et al. | |
| 2016/0000084 A1 | 1/2016 | Bickers et al. | |

FOREIGN PATENT DOCUMENTS

| | | |
|---|---|---|
| JP | 2001-500424 A | 1/2001 |
| JP | 4219711 B2 | 2/2009 |
| JP | 2016-510734 A | 4/2016 |
| WO | 2005094580 A1 | 10/2005 |
| WO | 2009095922 A1 | 8/2009 |
| WO | 2013111755 A1 | 8/2013 |

OTHER PUBLICATIONS

International Search Report issued in International Application No. PCT/JP2017/032452 dated Nov. 28, 2017 (2 pages).
Written Opinion issued in International Application No. PCT/JP2017/032452 dated Nov. 28, 2017 (4 pages).
International Search Report issued in International Application No. PCT/JP2016/089061 dated Feb. 28, 2017 (2 pages).
Written Opinion issued in International Application No. PCT/JP2016/089061 dated Feb. 28, 2017 (3 pages).
C. Yin et al.; "Synthesis of the Allantoin and Its Allelopathic Effects on Plants"; Journal of Yunnan University, vol. 21, pp. 327-328, p. 331; 1999 (5 pages).
H. Xu et al.; "Effect of Allantoin and Guangzengsu on Growth and Cold Tolerance of Rice Seedlings"; Guangxi Agricultural Sciences, No. 3, pp. 122-124; 1999 (6 pages).
H. Takagi et al.; "Allantoin, a stress-related purine metabolite, can activate jasmonate signaling in a MYC2-regulated and abscisic acid-dependent manner"; Journal of Experimental Botany, vol. 67, No. 8, pp. 2519-2532; Mar. 1, 2016 (14 pages).
D. V. Charlson et al.; "Allantoate amidohydrolase transcript expression is independent of drought tolerance in soybean"; Journal of Experimental Botany, vol. 60, No. 3, pp. 847-851; 2009 (5 pages).
S. Tanaka et al.; "Impact of allantoin accumulation on heat shock tolerance in *Arabidopsis*"; Abstract Book Annual Meeting of JSPP, PL-051 (0744), p. 317, Mar. 2016 (2 pages).
S. Watanabe et al.; "The purine metabolite allantoin enhances abiotic stress tolerance through synergistic activation of abscisic acid metabolism"; Plant, Cell and Environment, vol. 37, pp. 1022-1036; 2014 (15 pages).
Y. Sakuma et al.; "Dual function of an *Arabidopsis* transcription factor DREB2A in water-stress-responsive and heat-stress-responsive gene expression"; PNAS, vol. 103, No. 49, pp. 18822-18827; Dec. 5, 2006 (6 pages).
H. Sato et al.; "*Arabidopsis* DPB3-1, a DREB2A Interactor, Specifically Enhances Heat Stress-Induced Gene Expression by Forming a Heat Stress-Specific Transcriptional Complex with NF-Y Subunits"; The Plant Cell, vol. 26, pp. 4954-4973; Dec. 2014 (23 pages).
Y. Sakuma et al.; "Functional Analysis of an *Arabidopsis* Transcription Factor DREB2A, Involved in Drought-Responsive Gene Expression"; The Plant Cell, vol. 18, pp. 1292-1309; May 2006 (19 pages).
S. Watanabe et al.; "Verification of the Growth Promoting Effect of Allantoin, a Purine Degradation Intermediate for *Arabidopsis* Seedlings"; Abstracts of the 55th Annual Meeting of the Japanese Society of Plant Physiologists, PF044 (0461), p. 259; Mar. 11, 2014 (4 pages).
M. S. M. Al-Nimer et al.; "Ultraviolet light assisted extraction of flavonoids and allantoin from aqueous and alcoholic extracts of Symphytum othcinale"; Journal of Intercultural Ethnopharmacology, vol. 6, issue 3, pp. 280-283; 2017 (4 pages).
C. Staiger; "Comfrey: A Clinical Overview"; Phytotherapy Research, vol. 26, pp. 1441-1448; 2012 (8 pages).
Akema Fine Chemicals; "Allantoin, A safe and effective skin protectant"; 2006 (13 pages).

\* cited by examiner

COMPOSITION COMPRISING ALLANTOIN AND METHOD OF APPLYING ALLANTOIN TO A PLANT

CROSS-REFERENCE TO RELATED APPLICATIONS

This application is a continuation-in-part application of International Patent Application No. PCT/JP2016/089061 filed on Dec. 28, 2016 and International Patent Application No. PCT/JP2017/032452 filed on Sep. 8, 2017. PCT/JP2016/089061 claims the benefit of priority to Japanese Patent Application No. 2016-016383 filed on Jan. 29, 2016 and the benefit of priority to Japanese Patent Application No. 2016-043503 filed on Mar. 7, 2016. PCT/JP2017/032452 claims the benefit of priority to Japanese Patent Application No. 2016-175752 filed on Sep. 8, 2016. The contents of the priority applications are incorporated by reference in their entirety.

TECHNICAL FIELD

The present disclosure relates to a high temperature stress resistance-improving agent, a method for improving high temperature stress resistance, a whitening suppressor, and a DREB2A gene expression promoting agent of a plant.

The present disclosure also relates to a method for suppressing the growth of a gramineous plant such as turf grass and rice, and a gramineous plant growth suppressing agent. The present disclosure also relates to a method for producing a gramineous plant.

BACKGROUND

Plants are exposed to a wide variety of environmental stress, such as high temperature and dehydration.

The dehydration stress responsive element (DRE) is a sequence originally verified by promoter analysis of RD29A as a water stress inducible gene in the genome of *Arabidopsis thaliana*. The DRE binding protein (DREB) is a transcription factor isolated as a protein that binds to DRE. Among DREBs, DREB2A is an *APETALA2*/ethylene responsive element-binding factor-type (AP2/ERF-type) transcription factor, which was isolated as a DRE-recognizing protein (Sato, H., Plant Cell 26: 4954-4973, 2014). Since DREB2A is strongly induced by dehydration stress and high salt concentration stress, DREB2A is considered to be a transcription factor that functions under dehydration stress and high temperature stress conditions (Sakuma, Y. et al., Proc. Natl. Acad. Sci., U.S.A., 103: 18822-18827, 2006). DREB2A activity is post-translationally regulated, and a region of 30 amino acids adjacent to the AP2/ERF DNA binding domain is considered to play a key role in post-translational protein regulation. DREB2A CA, which is derived from DREB2A via deletion of such region, still has the activity, and DREB2A CA-overexpressing *Arabidopsis thaliana* exhibits a dwarf phenotype. Thus, DREB2A CA has been verified to improve dehydration stress resistance to a significant extent (Sakuma. Y. et al., Plant Cell 18: 1292-1309, 2006).

Sato, H., Plant Cell 26: 4954-4973, 2014 and WO 2013/111755 each report the mechanism of a plant in which DREB2A induces a target gene when the plant receives high temperature stress. Sato, H., Plant Cell 26: 4954-4973, 2014 and WO 2013/111755 each propose the mechanism, such that a protein DPB3-1 (or NF-YC 10) interacts with DREB2A and induction of high temperature stress resistance gene expression is promoted by DREB2A. In addition, Sato. H., Plant Cell 26: 4954-4973, 2014 demonstrates that the DPB3-1/DREB2A interaction would not affect the expression of dehydration stress-inducible genes.

JP Patent No. 4219711 describes that a rooting rate is improved and the life of cut flower is prolonged in a transgenic plant into which the DREB2A gene is introduced.

Allantoin (5-ureidohydantoin) is an intermediate product that is an intermediate product generated during the process of degradation of nucleic acid bases (purine bases). In plant bodies, allantoin is generated from 5-hydroxyisouric acid with the aid of allantoin synthase (AS) and then degraded into allantoic acid with the aid of allantoinase (ALN).

Watanabe, S. et al., Plant Cell Environ., 37: 1022-1036, 2014 reports that an aln-1 mutant of *Arabidopsis thaliana*, in which the ALN gene was deleted, accumulated allantoin in the plant body and had higher dehydration/dry stress resistance than that of a wild-type plant. It also discloses that production of abscisic acid was promoted when allantoin was administered to wild-type *Arabidopsis thaliana*. Accordingly, it is considered that the promoted production of abscisic acid is related to the improvement of dehydration/dry stress resistance by allantoin.

Watanabe et al., Abstracts of the 55th Annual Meeting of the Japanese Society of Plant Physiologists. PF044 (0461), 2014 reports that plant growth was promoted via application of allantoin to *Arabidopsis thaliana*.

US 2010/0333237 discloses a method of protecting a plant from stress via application of ureide, such as allantoin, to a plant. US 2010/0333237 also discloses that a plant is damaged by oxidative stress upon environmental disturbance, such as droughts or coldness and that a plant is protected from damage since the scavenger pathway is promoted by high ureide concentration. However, dehydration stress resistance is different from high temperature stress resistance in a plant.

The mechanism of developing the dehydration stress resistance is different from that of the high temperature stress resistance. According to Sato, H., Plant Cell 26: 4954-4973, 2014, for example, the DPB3-1/DREB2A interaction is necessary in order to induce high temperature stress resistance by DREB2A as described above.

However, Sato, H., Plant Cell 26: 4954-4973, 2014 describes that such interaction is not correlated with induction of dehydration stress resistance. As is apparent from the foregoing description, a certain component that is capable of improving resistance to stress other than high temperature stress, such as dehydration stress, is not always capable of improving high temperature stress resistance. On the basis of the finding of the past such that allantoin has activity of improving resistance to several types of stress other than high temperature stress of a plant, accordingly, it is not possible to predict activity of allantoin concerning high temperature stress resistance.

The expression of DREB2A gene of a plant contributes to an improvement in resistance to various types of stress, such as high temperature stress resistance or dehydration stress resistance, as described above. In addition, the expression of DREB2A gene is known to exert advantageous effects such as an improved rooting rate or prolonged life of cut flower. However, a substance that is applied to a plant and capable of promoting the expression of DREB2A gene in the plant has not been reported in the past, although transgenic plants into which the DREB2A gene is introduced are described in WO 2013/111755.

The effect of allantoin on rice growth has also been reported. Kyo et al., Guangxi Agricultural Sciences, 1999, 3rd phase, pp. 122 to 124 discloses that, when rice seeds were immersed in a 300 mg/L allantoin solution for 24 hours, germinated, and then allowed to grow up to seedlings, the height of the seedlings, the number of roots, and the fresh weight of the seedlings increased as compared to a control sample being treated with water, promoting the growth of the rice.

Although Watanabe, S. et al., Plant Cell Environ., 37: 1022-1036, 2014 discloses that applying allantoin to *Arabidopsis thaliana* promotes production of abscisic acid, the relationship between abscisic acid and the plant growth has not been elucidated.

SUMMARY

One or more embodiments of the present invention include a method for cultivating a plant, comprising applying allantoin to a plant; exposing the plant to a temperature of about 30° C. or more for at least about 60 minutes; and growing the plant in a cultivation medium.

The present disclosure also relates to an allantoin composition and a method of applying allantoin to a plant, which may improve high temperature stress resistance of a plant, suppress whitening of a plant, and promote DREB2A gene expression in a plant. Thus, one or more embodiments of the present invention also include the following:

(1) A high temperature stress resistance-improving agent for improving the high temperature stress resistance of a plant, comprising allantoin as an active ingredient.

(2) The high temperature stress resistance-improving agent according to (1) above, which is used to suppress one or more selected from the group consisting of whitening of the plant due to high temperature stress, withering of the plant due to high temperature stress, and curling of plant leaves due to high temperature stress.

(3) The high temperature stress resistance-improving agent according to (1) or (2), which promotes the expression of DREB2A gene in the plant.

(4) A method for improving the high temperature stress resistance of a plant, comprising a step of applying the high temperature stress resistance-improving agent according to any one of (1) to (3) to the plant.

(5) The method according to (4) above, wherein the step comprises applying the high temperature stress resistance-improving agent to the plant before the plant receives stress.

(6) A whitening suppressor for suppressing whitening of a plant, comprising allantoin as an active ingredient.

(7) A DREB2A gene expression promoting agent for promoting the expression of DREB2A gene in a plant, comprising allantoin as an active ingredient.

(8) A method for suppressing whitening of a plant, comprising a step of applying the whitening suppressor according to (6) to a plant.

(9) A method for promoting the expression of DREB2A gene in a plant, comprising a step of applying the DREB2A gene expression promoting agent according to (7) to the plant.

(10) Use of allantoin for improving the high temperature stress resistance of a plant.

(11) Use of allantoin for suppressing whitening of a plant.

(12) Use of allantoin for promoting the expression of DREB2A gene in a plant.

The present disclosure also relates to an allantoin composition and a method of applying allantoin to a plant, which may suppress the growth of a gramineous plant such as a turf grass or rice. Thus, one or more embodiments of the present invention also include the following:

(1) A gramineous plant growth suppressing agent for suppressing the growth of a gramineous plant, comprising allantoin as an active ingredient.

(2) The gramineous plant growth suppressing agent according to the above (1), wherein the gramineous plant is a turf grass or rice.

(3) A method for suppressing the growth of a gramineous plant, comprising a step of applying a gramineous plant growth suppressing agent comprising allantoin as an active ingredient (the gramineous plant growth suppressing agent according to the above (1)) to a gramineous plant.

(4) The method according to the above (3), wherein the gramineous plant is a turf grass or rice.

(5) The method according to the above (3) or (4), wherein the gramineous plant growth suppressing agent is a liquid composition or a granular composition comprising allantoin as an active ingredient.

(6) The method according to any one of the above (3) to (5), wherein the gramineous plant is a turf grass, and the step comprises applying the gramineous plant growth suppressing agent to the turf grass, before initial mowing and/or in an interval between mowings.

(7) The method according to any one of the above (3) to (6), wherein the step comprises applying the gramineous plant growth suppressing agent to the gramineous plant, so that the applied dose of allantoin per cultivation area for 1 month is 0.1 to 13 $g/m^2$/month.

(8) The method according to the above (7), wherein the step comprises applying the gramineous plant growth suppressing agent to the gramineous plant dividedly over 2 to 10 times per month.

(9) A method for producing a gramineous plant, comprising a cultivation step of cultivating the gramineous plant, wherein the cultivation step comprises suppressing the growth of the gramineous plant by the method according to any one of the above (3) to (8).

(10) Use of allantoin for suppressing the growth of a gramineous plant.

(11) The use according to the above (10), wherein the gramineous plant is a turf grass or rice.

(12) The use according to the above (10) or (11), wherein the allantoin is in the form of a liquid composition or a granular composition comprising the allantoin as an active ingredient.

(13) The use according to any one of the above (10) to (12), wherein the gramineous plant is a turf grass, and the allantoin is applied to the turf grass, before initial mowing and/or in an interval between mowings, so as to suppress the growth of the gramineous plant.

(14) The use according to any one of the above (10) to (13), wherein the allantoin is applied to the gramineous plant, so that the applied dose of the allantoin per cultivation area for 1 month is 0.1 to 13 $g/m^2$/month, so as to suppress the growth of the gramineous plant.

(15) The use according to the above (14), wherein the allantoin is applied to the gramineous plant dividedly over 2 to 10 times per month, so that the total applied dose per month of the allantoin is as described above, thereby suppressing the growth of the gramineous plant.

BRIEF DESCRIPTION OF DRAWINGS

In FIG. 3, the upper photograph shows onions of the allantoin treatment group (viability: 33.3%) and the lower photograph shows onions of the water treatment group (viability: 0%).

In FIG. 4, the upper photograph shows *Brassica chinensis* komatsuna of the allantoin treatment group (viability: 100%) and the lower photograph shows *Brassica chinensis* komatsuna of the water treatment group (viability: 33.3%).

DETAILED DESCRIPTION OF EMBODIMENTS

Figure 1A:
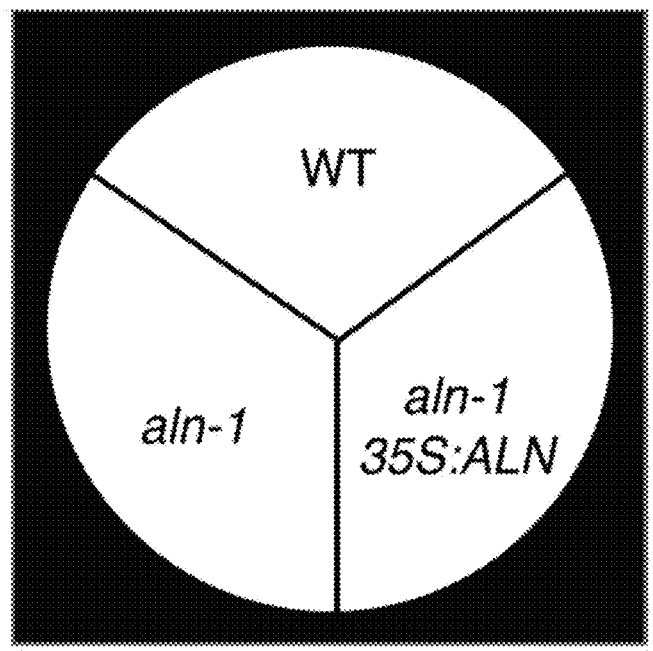
FIG. 1A illustrates compartments in a petri dish used in Experiment 1.

One or more embodiments of the present invention are described below.

1. Allantoin

Allantoin is also referred to as "5-ureidohydantoin," and the free form thereof has a structure represented by the formula below.

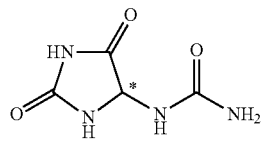 [SMILES: NC(=O)NC1NC(=O)NC1=O]

Allantoin has an asymmetric carbon (indicated by * in the formula), and it is either in the form of (R)-allantoin or (S)-allantoin. Allantoin used in the present disclosure may be (R)-allantoin or (S)-allantoin, or it may be in the form of a mixture of (R)-allantoin and (S)-allantoin. Allantoin may be synthetically produced, for example, from glyoxylic acid and urea. Allantoin may also be derived or obtained from plants such as comfrey and microorganisms.

Allantoin may be used in any form applicable to a plant. It may be the free form or any acceptable form such as solvate (e.g., a hydrate), salt, derivative, or complex thereof. It may be a mixture of two or more members of the free form, a hydrate, and any other form of allantoin.

2. Allantoin Composition

A composition according to the present disclosure comprises allantoin, which may be applied to a plant ("allantoin composition" or "allantoin-containing composition").

In one or more embodiments, a concentration of allantoin in the composition may be about 10 to 99% by weight. For example, the concentration may be about 10% by weight or more, about 20% by weight or more, about 30% by weight or more, about 40% by weight or more, about 50% by weight or more, about 60% by weight or more, about 70% by weight or more, about 80% or more, or about 90% by weight or more. The concentration may also be about 99% by weight or less, about 95% by weight or less, about 90% by weight or less, about 85% by weight or less, about 80% by weight or less, or about 75% by weight or less.

In one or more embodiments, the allantoin composition comprises one or more fertilizer components. The term "fertilizer component" as used herein refers to an element, a compound, or a composition utilized by plants, such as nitrogen, phosphorus, potassium, silicon, magnesium, calcium, manganese, boron, iron, and a compound or composition containing such an element. The fertilizer component may be organic or inorganic.

In one or more embodiments, a fertilizer component comprises a nitrogen source, a phosphorus source, a potassium source, a trace element, or a combination thereof. As a nitrogen source, ammonium sulfate, ammonium nitrate, ammonium chloride, urea, or lime nitrogen may be used. When a nitrogen source contains phosphorus and/or potassium, it may also serve as a phosphorus source and/or a potassium source.

As a phosphorus source, ammonium phosphate, potassium phosphate, superphosphate, triple superphosphate, fused phosphate fertilizer, multi-phosphate fertilizer, and phosphorous acid may be used. For example, ammonium phosphate includes monobasic ammonium phosphate (ammonium dihydrogen phosphate), ammonium secondary phosphate (diammonium hydrogen phosphate), and ammonium tertiary phosphate (triammonium phosphate). For example, potassium phosphate includes potassium primary phosphate (potassium dihydrogen phosphate) and potassium secondary phosphate (dipotassium hydrogen phosphate). When a phosphorus source contains nitrogen and/or potassium, it may also serve as a nitrogen source and/or a potassium source.

As a potassium source, potassium sulfate, potassium chloride, and potassium bicarbonate may be used. When a potassium source contains phosphorus and/or nitrogen, it may also serve as a phosphorus source and/or a nitrogen source.

As a trace element, boron, copper, iron, manganese, molybdenum, and zinc may be included. Examples of compounds providing such trace elements include boric acid, borax, copper sulfate, chelated copper, chelated iron, iron oxide, manganese sulfate, sodium molybdate, ammonium molybdate, zinc sulfate, and chelated zinc.

A fertilizer component may include the following: a fertilizer containing calcium, such as burnt lime, hydrated lime, magnesium lime, and calcium carbonate; a fertilizer containing silicon, such as calcium silicate: a slag silicate fertilizer; a fertilizer containing magnesium, such as magnesium sulfate, magnesium chloride, and humic acid magnesium; a fertilizer containing manganese, such as manganese sulfate, magnesium/manganese sulfate, and slag manganese; a fertilizer containing boron, such as boric acid and borate; a composite fertilizer containing trace elements; a fertilizer containing iron, such as iron/steel slag; or a fertilizer containing zinc, such as zinc sulfate.

In one or more embodiments, a concentration of a single fertilizer component in the allantoin composition may be 1% by weight or more, 2% by weight or more, 5% by weight or more, 10% by weight or more, 15% by weight or more, 20% by weight or more, 25% by weight or more, 30% or more, or 40% by weight or more. The concentration of a single fertilizer component may also be about 50% by weight or less, about 40% by weight or less, about 30% by weight or less, about 20% by weight or less, about 15% by weight or less, about 10% by weight or less, or about 5% by weight or less. For example, the concentration may be about 1 to 40% by weight, about 5 to 35% by weight, about 10 to 30% by weight, or about 15 to 25% by weight.

In one or more embodiments, a nitrogen content in the allantoin composition may be at least about 0.5% by weight. The term "nitrogen content" as used herein refers to a total content of nitrogen calculated as elemental nitrogen, which includes nitrogen derived from allantoin. The nitrogen content may be about 1% by weight or more, about 3% by weight or more, about 5% by weight or more, about 10% by weight or more, about 15% by weight or more, about 20% by weight or more, about 25% by weight or more, about 30% or more, or about 35% by weight or more. The nitrogen content may also be about 50% by weight or less, about 40% by weight or less, about 30% by weight or less, or about 20% by weight or less. For example, the nitrogen content may be about 1 to 40% by weight, about 5 to 35% by weight, about 10 to 30% by weight, or about 15 to 25% by weight.

In one or more embodiments, a phosphorus content in the allantoin composition may be at least about 0.5% by weight. The term "phosphorus content" as used herein refers to a total content of phosphorus or water-soluble phosphorus calculated as $P_2O_5$. The phosphorus content may be about 1% by weight or more, about 2% by weight or more, about 3% by weight or more, about 5% by weight or more, about 8% by weight or more, about 11% by weight or more, about 15% by weight or more, about 20% or more, or about 30% by weight or more. The phosphorus content may also be about 40% by weight or less, about 30% by weight or less, about 20% by weight or less, or about 10% by weight or less. For example, the phosphorus content may be about 1 to 30% by weight, about 3 to 25% by weight, about 5 to 20% by weight, or about 8 to 15% by weight.

In one or more embodiments, a potassium content in the allantoin composition may be at least about 0.5% by weight. The term "potassium content" as used herein refers to a total content of potassium or water-soluble potassium calculated as $K_2O$. The potassium content may be about 1% by weight or more, about 2% by weight or more, about 3% by weight or more, about 5% by weight or more, about 8% by weight or more, about 11% by weight or more, about 15% by weight or more, about 20% or more, or about 30% by weight or more. The potassium content may also be about 40% by weight or less, about 30% by weight or less, about 20% by weight or less, or about 10% by weight or less. For example, the potassium content may be about 1 to 30% by weight, about 3 to 25% by weight, about 5 to 20% by weight, or about 8 to 15% by weight.

In one or more embodiments, the allantoin composition may comprise an additive such as a surfactant and a binder. A concentration of the additive in the allantoin composition may be at least about 0.001% by weight. The additive concentration may be about 0.005% by weight or more, about 0.01% by weight or more, about 0.05% by weight or more, about 0.1% by weight or more, about 0.5% by weight or more, about 1% by weight or more, about 3% by weight or more, about 5% or more, or about 10% by weight or more. The additive concentration may also be about 30% by weight or less, about 20% by weight or less, about 15% by weight or less, or about 10% by weight or less. For example, the additive concentration may be about 0.01 to 20% by weight, about 0.05 to 15% by weight, about 0.1 to 10% by weight, or about 0.5 to 5% by weight.

Examples of such additives include polymeric compounds, non-polymeric compounds, salts thereof, and combinations of one or more additives. The polymeric compounds include carboxymethyl cellulose, methyl cellulose, ethyl cellulose, polyvinyl pyrrolidone, pullulan, acrylic acid-based polymer, polyvinyl alcohol, gelatin, agar, gum arabic, gum arabic powder, xanthan gum, trant gum, guar gum, gellan gum, locust bean gum, partially pregelatinized starch, macrogol, starch, soluble starch, dextrin, tragacanth gum, β-glucan, pectin, casein, soybean protein, hydroxyethyl cellulose, acetylcellulose, lignin sulfonic acid, carboxymethyl starch, hydroxyethyl starch, polyvinyl methyl ether, hydroxypropyl cellulose, hydroxypropyl methyl cellulose, polyethylene glycol, polyethylene oxide, polyvinylpyrrolidone, shellac, rosin, tall oil, ester gum, polyvinyl acetate, polylactic acid, polyvinyl chloride, polyester, polyurea, polyamide, cumarone resin, biodegradable polymers, paraffin wax, microcrystalline wax, petrolatum, montan wax, carnauba wax, cotton wax, beeswax, wool wax, non-ionic polymeric surfactant, anionic polymeric surfactant, cationic polymeric surfactant, amphoteric polymeric surfactant, and alginic acid. The non-polymeric compounds include sodium silicate, glycerin, vegetable and animal oils, fat and oil, liquid paraffin, fuel oil, glucose, sucrose, mannitol, sorbitol, non-polymeric non-ionic surfactant, non-polymeric anionic surfactant, non-polymeric cationic surfactant, and non-polymeric amphoteric surfactant.

In one or more embodiments, the allantoin composition may be a solid form. The solid formulation may be in the form of granules, powder, tablets, or flowable formulations. The solid formulation may have a water content of about 5% by weight or less, about 3% by weight or less, about 1% by weight or less, about 0.5% by weight or less, about 0.1% by weight or less, about 0.05% by weight or less, or about 0.01% by weight or less.

In one or more embodiments, a granular or powder composition comprising allantoin may have an average diameter of about 1 μm or more, about 10 μm or more, about 50 μm or more, or about 100 μm or more. The average diameter may also be about 1,000 μm or less, about 500 μm or less, about 200 μm or less, or about 100 μm or less.

In one or more embodiments, the allantoin composition may be a liquid form. The liquid formulation may comprise allantoin at a concentration of about 10 to 5,000 ppm, about 100 to 2,000 ppm, or about 300 to 1,500 ppm. The concentration may be about 10 ppm or more, about 50 ppm or more, about 100 ppm or more, about 300 ppm or more, about 500 ppm or more, or about 1,000 ppm or more, and may also be about 5,000 ppm or less, about 4,000 ppm or less, about 3,000 ppm or less, about 2,000 ppm or less, about 1,500 ppm or less, or about 1,000 ppm or less.

In one or more embodiments, the liquid formulation may have the pH of about 7.0 or less. For example, the pH of the liquid formulation may be about 6.5 or less, about 5.0 or less, about 4.5 or less, about 4.0 or less, about 3.5 or less, or about 3.0 or less. The pH of the liquid formulation may also be about 2.0 or more, about 2.5 or more, about 3.0 or more, about 3.5 or more, about 4.0 or more, or about 4.5 or more. The pH of the liquid formulation may be, for example, about 3.0 to 7.0, about 3.5 to 6.5, about 4.0 to 6.0, or about 4.5 to 5.5.

In one or more embodiments, the liquid formulation may be prepared by dissolving the solid formulation into water or an aqueous solution. For example, a concentration of the solid composition in the liquid formulation may be about 5% by weight or less, about 3% by weight or less, about 1% by weight or less, about 0.5% by weight or less, about 0.1% by weight or less, or about 0.05% by weight or less. The concentration of the solid composition in the liquid formulation may also be about 0.001% by weight or more, about 0.005% by weight or more, about 0.01% by weight or more, about 0.05% by weight or more, about 0.1% by weight or more, or about 0.5% by weight or more.

The liquid formulation may comprise one or more components of the solid formulation according to one or more embodiments of the present invention.

In one or more embodiments, the allantoin composition may comprise one or more pesticides such as chemical pesticides and biological pesticides. Such pesticides include herbicides, germicides, fungicides, insecticides, and pest attractant substances.

3. Method of Applying Allantoin to Plants

In one or more embodiments, allantoin or the allantoin composition may be applied to a plant at various concentrations. For example, the dose of allantoin (per cultivation area per month) may be about 0.05 $g/m^2$/month or more, about 0.1 $g/m^2$/month or more, about 0.2 $g/m^2$/month or more, about 0.3 $g/m^2$/month or more, about 0.4 $g/m^2$/month or more, about 0.5 $g/m^2$/month or more, about 0.6 $g/m^2$/month or more, about 0.7 $g/m^2$ month or more, about 0.8 $g/m^2$/month or more, about 0.9 $g/m^2$/month or more, about 1 $g/m^2$/month or more, about 1.5 $g/m^2$/month or more, about 3 $g/m^2$/month or more, about 5 $g/m^2$/month or more, or about 10 $g/m^2$/month or more. The dose of allantoin per cultivation area per month may also be about 20 $g/m^2$/month or less, about 13 $g/m^2$/month or less, about 10 $g/m^2$/month or less, about 8 $g/m^2$/month or less, about 6 $g/m^2$/month or less, about 5 $g/m^2$/month or less, about 4 $g/m^2$/month or less, about 3 $g/m^2$/month or less, about 2 $g/m^2$/month or less, about 1.5 $g/m^2$/month or less, about 1 $g/m^2$/month or less, about 0.8 $g/m^2$/month or less, or about 0.6 $g/m^2$/month or less.

For example, the dose of allantoin may be about 0.05 to 20 $g/m^2$/month, about 0.1 to 13 $g/m^2$/month, about 1 to 10 $g/m^2$/month, or about 3 to 8 $g/m^2$/month. The dose may also be about 0.05 to 5 $g/m^2$/month, 0.1 to 3 $g/m^2$/month, or 0.2 to 1.5 $g/m^2$/month.

In one or more embodiments, a concentration of allantoin in a cultivation medium may be about 10 μM or more, about 50 μM or more, about 100 μM or more, about 250 μM or more, about 500 μM or more, about 750 μM or more, about 1 mM or more, about 1.25 mM or more, about 1.5 mM or more, about 3 mM or more, about 6 mM or more, about 10 mM or more, about 20 mM or more, about 30 mM, or about 50 mM or more. The concentration of allantoin may also be about 100 mM or less, about 50 mM or less, about 30 mM or less, about 20 mM or less, about 10 mM or less, about 8 mM or less, about 6 mM or less, about 4 mM or less, about 2 mM or less, about 1 mM or less, about 800 μM or less, or about 600 μM or less.

For example, the concentration of allantoin may be about 10 μM to 100 mM, about 100 μM to 50 mM, about 500 μM to 30 mM, or about 1 mM to 20 mM.

In one or more embodiments, plants may be grown in cultivation media before or after applying allantoin or the allantoin composition to the plants. Plants may also be hydroponically grown. Such cultivation media include, but are not limited to soil, water, and a cultivation material.

In one or more embodiments, allantoin or the allantoin composition may be applied to the whole plant or a part of the plant. For example, allantoin or the allantoin composition may be applied directly to a plant body, such as roots, stems, leaves, branches, flowers, fruiting bodies, fruits, seeds, tubers, rhizomes, and any other parts of a plant. Allantoin or the allantoin composition may also be applied to a plant through cultivation media or a surrounding environment such as a crop field.

In one or more embodiments, allantoin or the allantoin composition may be provided through various methods such as foliar application, fertigation, and soil application. Such application methods include, but are not limited to spraying, misting, dusting, dressing, coating, dust coating, diffusion, dipping, irrigation, injection, sprinkling, foaming, fumigation, smoking, fuming, spreading, and painting. For example, allantoin or the allantoin composition, such as the liquid formulation, may be sprayed over cultivation media, or sprayed onto plants. Types of irrigation include, but are not limited to surface irrigation, micro-irrigation, sprinkler irrigation such as center pivot irrigation, and subirrigation.

Allantoin or the allantoin composition may be applied using a machine, a device, or equipment such as drones, helicopters, sprinklers, and center pivots.

In one or more embodiments, allantoin or the allantoin composition may also be mixed in cultivation media. For example, the liquid formulation may be applied to plant roots via surface irrigation or the solid formulation may be added to soil.

In one or more embodiments, a spreading agent may be used together with allantoin or the allantoin composition. Examples of the spreading agent include various surfactants such as sodium dialkyl sulfosuccinate, polyoxyethylene alkyl ether, polyoxyethylene alkylphenyl ether, polyoxyethylene fatty acid ester. The spreading agent may also be paraffin, terpene, polyamide resin, polyacrylate, polyoxyethylene, wax, polyvinyl alkyl ether, alkylphenol formalin condensate, and synthetic resin emulsion.

In one or more embodiments, allantoin or the allantoin composition may be applied together with one or more pesticides such as chemical pesticides and biological pesticides. Such pesticides include herbicides, germicides, fungicides, insecticides, and pest attractant substances. The pesticides and allantoin may be mixed in a composition such as the liquid formulation according to one or more embodiments of the present invention. The pesticides may also be applied to plants either simultaneously or at any time before or after applying allantoin or the allantoin composition to the plants.

In one or more embodiments, allantoin or the allantoin composition may be applied several times by dividing a total amount to be applied. For example, allantoin or the allantoin composition may be applied 2 times or more per month, 3 times or more per month, 4 times or more per month, or 5 times or more per month. It may be applied less than 10 times per month, less than 8 times per month, less than 6 times per month, or less than 4 times per month. Time intervals between each application may be 0.5 days or more, 1 day or more, 2 days or more, 3 days or more, 5 days or more, or 10 days or more, and may also be 15 days or less, 10 days or less, 5 days or less, 3 days or less, or 2 day or less. For example, time intervals may be 0.5 to 10 days, 0.5 to 9 days, 0.5 to 8 days, 0.5 to 7 days, 0.5 to 6 days, 0.5 to 5 days, 0.5 to 4 days, 0.5 to 3 days, 0.5 to 2 days, or 0.5 to 1.5 days.

Allantoin or the allantoin composition may be applied to a plant at any growth phase. In one or more embodiments, allantoin or the allantoin composition may be applied to a plant at a germination stage, a vegetative stage, a reproductive stage, a flowering stage, or a ripening stage. In one or more embodiments, allantoin or the allantoin composition may be applied to a plant grown for, for example, 1 day or more, 3 days or more, 5 days or more, 10 days or more, 15 days or more, 20 days or more, 25 days or more, 30 days or more, 40 days or more, 50 days or more, 60 days or more, 70 days or more, 80 days or more, 90 days or more, 100 days or more, 110 days or more, 120 days or more, 150 days or more, 180 days or more, 240 days or more, 1 year or more, 1.5 years or more, 2 years or more, or 2.5 years or more, after seeding the plant.

In one or more embodiments, allantoin or the allantoin composition may be applied to a annual plant, a biennial plant, or a perennial plant. Allantoin or the allantoin composition may be applied to various plants as described herein.

In one or more embodiments, plants may be cultivated under various conditions and in various climates before or after applying allantoin or the allantoin composition. Plants may be grown or cultivated in cultivation media for 1 day or more, 3 days or more, 5 days or more, 10 days or more, 15 days or more, 20 days or more, 25 days or more, 30 days or more, 40 days or more, 50 days or more, 60 days or more, 70 days or more, 80 days or more, 90 days or more, 100 days or more, 110 days or more, 120 days or more, 150 days or more, 180 days or more, 240 days or more, 1 year or more, 1.5 years or more, 2 years or more, or 2.5 years or more. Plants may also be grown or cultivated in cultivation media for 3 years or less, 2.5 years or less, 1.5 years or less, 1 year or less, 240 days or less, 180 days or less, 150 days or less, 120 days or less, 110 days or less, 100 days or less, 90 days or less, 80 days or less, 70 days or less, 60 days or less, 50 days or less, 40 days or less, 30 days or less, 25 days or less, 20 days or less, 15 days or less, 10 days or less, 5 days or less, or 3 days or less.

Plants may be grown or cultivated at a temperature of about 5° C. or higher, about 10° C. or higher, about 15° C. or higher, about 20° C. or higher, about 25° C. or higher, about 27.5° C. or higher, about 30° C. or higher, about 32.5° C. or higher, about 35° C. or higher, about 37.5° C. or higher, about 40° C. or higher, about 42.5° C. or higher, or about 45° C. or higher. Plants may also be grown at a temperature of about 50° C. or less, about 45° C. or less, about 40° C. or less, about 35° C. or less, about 30° C. or less, about 25° C. or less, about 20° C. or less, about 15° C. or less, or about 10° C. or less. The temperature may be a temperature of a cultivation medium such as a soil temperature.

Plants may be exposed to such temperatures for various time ranges. In one or more embodiments, an exposure time per day may be about 30 minutes or more, about 60 minutes or more, about 90 minutes or more, about 120 minutes or more, about 180 minutes or more, about 240 minutes or more, about 300 minutes or more, or about 360 minutes or more. An exposure time may also be about 600 minutes or more, about 480 minutes or less, about 360 minutes or less, about 240 minutes or less, about 180 minutes or less, about 120 minutes or less, or about 60 minutes or less.

The number of exposure days per year may be 1 or more, 5 or more, 10 or more, 20 or more, 30 or more, 60 or more, 90 or more, 120 or more, 150 or more, or 180 or more. The number of exposure days per year may also be 210 or less, 180 or less, 150 or less, 120 or less, 90 or less, 60 or less, 30 or less, 20 or less, 10 or less, or 5 or less.

4. Plants

In one or more embodiments, allantoin, an allantoin-containing composition, a high temperature stress resistance-improving agent, a whitening suppressor, or a DREB2A gene expression promoting agent may be applied to target plants. The target plants are not particularly limited, and examples thereof include various plants, such as dicotyledons and monocotyledons.

Examples of dicotyledons, to which allantoin, an allantoin-containing composition, a high temperature stress resistance-improving agent, a whitening suppressor, or a DREB2A gene expression promoting agent is applied, include plants of *Pharbitis, Brassica, Convolvulus, Ipomoea, Arabidopsis thaliana, Cuscuta, Dianthus, Stellaria, Minuartia, Cerastium, Sagina japonica, Arenaria, Moehringia, Pseudostellaria, Honkenya, Spergula, Silene, Lychnis, Silene firma*, Caryophyllaceae, Casuarinaceae, Saururaceae, Piperaceae, Chloranthaceae, Salicaceae, Myricaceae, Juglandaceae, Betulaceae, Fagaceae, Ulmaceae, Moraceae, Urticaceae, Podostemaceae, Proteaceae, Olacaceae, Santalaceae, Loranthaceae, Arisiolochiaceae, Rafflesiaceae, Balanophoraceae, Polygonaceae, Chenopodiaceae, Amaranthaceae, Nyctaginaceae, Theligonaceae, Phytolaccaceae, Aizoaceae, Portulacaceae, Magnoliaceae, Trochodendraceae, Cercidiphyllaceae, Nymphaeaceae, Ceratophyllaceae, Ranunculaceae, Lardizabalaceae, Berberidaceae, Menispermaceae, Calycanthaceae, Lauraceae, Papaveraceae, Capparaceae, Brassicaceae, Droseraceae, Nepenihaceae, Crassulaceae, Saxifragaceae, Pittosporaceae, Hamamelidaceae, Platanaceae, Rosaceae, Leguminosae, Oxalidaceae, Geraniaceae, Linaceae, Zygophyllaceae, Rutaceae, Simaroubaceae, Meliaceae, Polygalaceae, Euphorbiaceae, Callitrichaceae, Buxaceae, Empetraceae, Coriariaceae. Anacardiaceae, Aquifoliaceae, Celastraceae, Staphyleaceae, Icacinaceae, Aceraceae, Hippocastanaceae, Sapindaceae, Sabiaceae, Balsaminaceae, Rhamnaceae, Vitaceae, Elaeocarpaceae, Tiliaceae, Malaceae, Sterculiaceae, Dilleniaceae, Theaceae, Guttlferae, Elatinaceae, Tamaricaceae, Violaceae, Flacourtiaceace, Stachyuraceae, Passifloraceae, Begoniaceae, Cactaceae. Thymelaeaceae, Elaeagnaceae, Lythraceae, Punicaceae, Rhizophoraceae, Alangiaceae, Melastomataceae, Trapaceae, Onagraceae, Haloragaceae, Hippuridaceae, Araliaceae, Umbelliferae, Cornaceae, Diapensiaceae, Clethraceae, Pyrolaceae, Ericaceae, Myrsinaceae, Primulaceae, Plumbaginaceae, Ebenaceae, Symplocaceae, Styracaceae, Oleaceae, Buddlejaceae, Gentianaceae, Apocynaceae, Asclepiadaceae, Polemoniaceae, Boraginaceae, Verbenaceae, Lamiaceae, Solanaceae, Scrophulariaceae, Bignoniaceae, Pedaliaceae, Orobanchaceae, Gesneriaceae, Lentibulariaceae, Acanthaceae, Myoporaceae, Phrymaceae, Plantaginaceae, Rubiaceae, Caprifoliaceae, Adoxaceae, Valerianaceae, Dipsacaceae, Cucurbitaceae, Campanulaceae, and Asteraceae.

Examples of monocotyledons, to which allantoin, an allantoin-containing composition, a high temperature stress resistance-improving agent, a whitening suppressor, or a DREB2A gene expression promoting agent is applied, include plants of *Spirodela, Lemna, Cattleya, Cymbidium, Dendrobium, Album, Phalaenopsis, Vanda, Paphiopedilum*, Orchidaceae, Typhaceae, Sparganiaceae, Potamogetonaceae, Najadaceae, Scheuchzeriaceae, Alismataceae, Hydrocharitaceae, Triuridaceae, Cyperaceae, Palmae, Araceae, Eriocaulaceae, Commelinaceae, Pontederiaceae, Juncaceae, Stemonaceae, Liliaceae, Amaryllidaceae, Dioscoreacea, Iridaceae, Musaceae, Zingiberaceae, Cannaceae, and Burmanniaceae.

Examples of the target plants also include rice, corn or maize, wheat, barley, sugarcane, sorghum, soybean, cotton, lettuce, tomato, almond, nuts, coffee, and pepper.

In one or more embodiments, one or more plants mentioned above may be excluded from the target plants.

Target plants are not limited to wild-type plants, and mutants, transformants, genetically-modified plants or crops, and any other type of plants may be the target plants.

5. Improvement of High Temperature Stress Resistance of Plants

In one or more embodiments, a high temperature stress resistance-improving agent comprises allantoin as an active ingredient and increases the high temperature stress resistance of a plant.

In one or more embodiments, a method for improving the high temperature stress resistance of a plant comprises a step of applying the high temperature stress resistance-improving agent to a plant.

The term "high temperature stress" used herein refers to stress induced when a plant is exposed to a temperature higher than normal growth temperatures, such as about 25° C. or higher. The stress inducing temperature may be about 27.5° C. or higher, about 30° C. or higher, about 32.5° C. or higher, about 35° C. or higher, about 37.5° C. or higher, about 40° C. or higher, about 42.5° C. or higher, or about 45° C. or higher, and may be about 50° C. or less. The temperature may be a temperature of a cultivation medium such as a soil temperature. The heat stress resistant plant may have increased viability and productivity. Therefore, one or more embodiments of the present invention also relate to a method for increasing plant productivity.

The exposure time per day, during which a plant is exposed to such high temperature, is not particularly limited. For example, such duration can be about 30 minutes or longer, about 60 minutes or longer, about 90 minutes or longer, about 120 minutes or longer, about 180 minutes or longer, about 240 minutes or longer, about 300 minutes or longer, or about 360 minutes or longer, and it can be about 600 minutes or less. The number of exposure days per year may be 1 or more, 2 or more, 3 or more, 4 or more, 5 or more, 6 or more, 7 or more, 10 or more, 15 or more, 20 or more, 25 or more, 30 or more, 40 or more, 50 or more, 60 or more, or 70 or more, and may also be 90 or less.

In one or more embodiments, the high temperature stress resistance-improving agent and the method for improving high temperature stress resistance of a plant can improve or increase resistance to high temperature stress. Such agent and method can improve or increase resistance to stress in a plant when the plant is exposed to sufficient humidity and high temperature.

In general, when a plant is exposed to a high temperature stress environment, physiological damages, such as whitening (chlorosis) of a plant, withering of a plant, or curling of leaves, may occur. In one or more embodiments, the high temperature stress resistance-improving agent and the method for improving high temperature stress resistance may suppress one or more physiological damages described above. In the experiments described herein, among the physiological damages induced by high temperature stress, at least one of whitening induced by high temperature stress (i.e., chlorosis), withering induced by high temperature stress, and curling of plant leaves induced by high temperature stress was suppressed by the high temperature stress resistance-improving agent and the method for improving high temperature stress resistance.

In one or more embodiments of the high temperature stress resistance-improving agent and the method for improving high temperature stress resistance, a mechanism of allantoin for improving high temperature stress resistance is not particularly limited. In one or more embodiments, high temperature stress resistance is improved by promoting the expression of DREB2A gene in the plant. Promotion of the expression of DREB2A gene is described in detail in "7. Promoting DREB2A gene expression" below.

In one or more embodiments of the high temperature stress resistance-improving agent and the method for improving high temperature stress resistance, high temperature stress resistance may be improved by promoting the expression of DREB2A gene in a plant and suppressing the expression of the heat shock transcription factor 3 (HSF3) gene. According to Sakuma, Y. et al., Proc. Natl. Acad. Sci., U.S.A., 103: 18822-18827, 2006, in *Arabidopsis thaliana* in which DREB2A CA is overexpressed, the HSF3 gene expression level is increased, and high temperature stress resistance is then improved. In one or more embodiments, the DREB2A gene expression level is increased upon application of allantoin to a plant while the HSF3 gene expression level is suppressed and high temperature stress resistance is improved. Accordingly, allantoin may improve high temperature stress resistance of a plant via the mechanism that is different from mechanisms that have been known in the past. Suppression of the HSF3 gene expression is described in detail in "7. Promoting DREB2A gene expression" below.

In one or more embodiments, the high temperature stress resistance-improving agent contains allantoin and is capable of improving high temperature stress resistance of a plant. The agent may be allantoin itself or a composition comprising allantoin and other components. The high temperature stress resistance-improving agent may contain allantoin in an amount effective for improving high temperature stress resistance of a plant.

The high temperature stress resistance-improving agent may be in any form, such as a solid or liquid.

In one or more embodiments, when the high temperature stress resistance-improving agent is an allantoin-containing composition, the composition may further contain other components useful for plants and components necessary for preparation of the agent. Examples of other components include fertilizer components. Examples of components necessary for preparation of the agent include carriers and liquid media.

In one or more embodiments, when the high temperature stress resistance-improving agent is an allantoin-containing composition, a method for producing the same is not particularly limited. For example, the agent can be produced by mixing components. In the case of a solid composition, according to need, operation, such as grinding, granulation, or dehydration, may be performed. In the case of a liquid composition, according to need, operation, such as stirring or dispersion, may be performed.

In one or more embodiments, the method for improving the high temperature stress resistance of a plant comprises a step of applying the high temperature stress resistance-improving agent to a plant. The method may be applied to any plants in need of improved high temperature stress resistance. Examples thereof include plants that are cultivated under conditions in which plants may receive high temperature stress as described above. Specific plant species are also described above.

In one or more embodiments, a method of applying the high temperature stress resistance-improving agent to a plant is not particularly limited, and the high temperature stress resistance-improving agent or allantoin released from the high temperature stress resistance-improving agent may be brought into contact with a part of a plant, such as a root, a stem, or a leaf of a plant. The high temperature stress resistance-improving agent may be directly applied to the plant, or may be applied to a cultivation medium, such as soil, in which the plant is fixed. In one or more embodiments of the present invention, the high temperature stress resistance-improving agent can be applied to a plant in such a manner that allantoin is applied to the plant in an amount effective for improving high temperature stress resistance.

In one or more embodiments, although the timing of applying the high temperature stress resistance-improving agent to a plant is not particularly limited, the agent may be applied to the plant before the plant receives high temperature stress. In one or more embodiments, the high temperature stress resistance-improving agent promotes the expression of DREB2A gene. As described above, expression of various stress resistant genes may be induced upon the expression of DREB2A gene. Accordingly, a plant, to which the high temperature stress resistance-improving agent is applied before the plant receives high temperature stress, may achieve high temperature stress resistance in advance, and may increase its viability upon the plant receives high temperature stress.

In one or more embodiments, when the high temperature stress resistance-improving agent is applied to the plant before the plant receives high temperature stress, the time point at which the high temperature stress resistance-improving agent is applied to the plant is designated as "T1" and the time point at which exposure of the plant to high temperature stress is initiated is designated as "T2." In such a case, the period from T1 to T2 may be 0.5 to 10 days, 0.5 to 9 days, 0.5 to 8 days, 0.5 to 7 days, 0.5 to 6 days, 0.5 to 5 days, 0.5 to 4 days, 0.5 to 3 days, 0.5 to 2 days, or 0.5 to 1.5 days. In such embodiments, the plant having the high temperature stress resistance improved through application of the agent is exposed to high temperature stress. Thus, the viability after the plant is exposed to high temperature stress can high. The high temperature stress resistance-improving agent may be applied to the plant N times (N is 2 or greater) before the plant receives high temperature stress. In such a case, the period from $T1_n$ ($n$ is an integer of 1 to N) at which the high temperature stress resistance-improving agent is applied to T2 may be within the range described above. In one or more embodiments, applying the high temperature stress resistance-improving agent a plurality of times can further improve the high temperature stress resistance of the plant.

6. Suppression of Plant Whitening

In one or more embodiments, a whitening suppressor for suppressing whitening of a plant comprises allantoin as an active ingredient.

In one or more embodiments, a method for suppressing whitening of a plant comprises a step of applying the whitening suppressor to a plant.

Whitening of a plant is also referred to as "chlorosis," and it is caused primarily by high temperature stress.

In one or more embodiments, the method may be applied to any plants in need of whitening suppression. Examples thereof include plants that are cultivated in the environment in which plants may be exposed to high temperature stress, such as the temperature conditions as described above. Specific plant species are also described above.

In one or more embodiments, the whitening suppressor contains allantoin and is capable of suppressing whitening of a plant. The agent may be allantoin itself or a composition comprising allantoin and other components. The whitening suppressor may contain allantoin in an amount effective for whitening suppression of a plant.

The whitening suppressor of the present invention may be in any form, such as a solid or liquid.

In one or more embodiments, when the whitening suppressor is an allantoin-containing composition, the composition can be the same allantoin-containing composition as the high temperature stress resistance-improving agent described above.

In one or more embodiments, a method of applying the whitening suppressor to a plant is not particularly limited, and the whitening suppressor or allantoin released from the whitening suppressor may be brought into contact with a part of a plant, such as a root, a stem, or a leaf of a plant. The whitening suppressor may be directly applied to the plant, or may be applied to a cultivation medium, such as soil in which the plant is fixed. In one or more embodiments of the present invention, the whitening suppressor can be applied to a plant in such a manner that allantoin is applied to the plant in an amount effective for whitening suppression.

In one or more embodiments, although the timing of applying the whitening suppressor to a plant is not particularly limited, the whitening suppressor may be applied to the plant before the plant receives stress causing whitening (e.g., high temperature stress). In one or more embodiments, the whitening suppressor promotes the expression of DREB2A gene. As described above, expression of various stress resistant genes may be induced upon the expression of DREB2A gene. Accordingly, a plant, to which the whitening suppressor is applied before the plant receives stress, may achieve stress resistance in advance, and whitening caused upon the plant receives stress may be suppressed effectively.

In one or more embodiments, when the whitening suppressor is applied to the plant before the plant receives stress causing whitening, the time point at which the whitening suppressor is applied to the plant is designated as "T1" and the time point at which exposure of the plant to the stress is initiated is designated as "T2." In such a case, the period from T1 to T2 may be 0.5 to 10 days, 0.5 to 9 days, 0.5 to 8 days, 0.5 to 7 days, 0.5 to 6 days, 0.5 to 5 days, 0.5 to 4 days, 0.5 to 3 days, 0.5 to 2 days, or 0.5 to 1.5 days. In such embodiments, the plant having the stress resistance improved through application of the whitening suppressor is exposed to the stress. Thus, whitening may be suppressed more effectively. The whitening suppressor may be applied to the plant N times (N is 2 or greater) before the plant receives stress. In such a case, the period from $T1_n$ ($n$ is an integer of 1 to N) at which the whitening suppressor is applied to T2 may be within the range described above. In one or more embodiments, applying the whitening suppressor a plurality of times can suppress whitening of a plant more effectively.

7. Promoting DREB2A Gene Expression

In one or more embodiments, a DREB2A gene expression promoting agent for promoting the expression of DREB2A gene in a plant comprises allantoin as an active ingredient.

In one or more embodiments, a method of promoting the expression of DREB2A gene in the plant comprises a step of applying the DREB2A gene expression promoting agent to a plant.

One or more embodiments of the present invention improve resistance to various types of stress, such as high temperature stress resistance or dehydration stress resistance, by promoting the expression of DREB2A gene in a plant. One or more embodiments of the present invention exhibit advantageous effects, such as an improved rooting rate or a prolonged life of cut flower, of a target plant.

In one or more embodiments, the method of promoting the expression of DREB2A gene in the plant may suppress the expression of HSF3 gene.

In the present disclosure, the term "gene expression" includes a process of mRNA expression using genomic DNA as a template (i.e., transcription) and/or a process of protein synthesis using the mRNA as a template (i.e., translation). The term "gene" used in the present disclosure refers to a nucleic acid comprising a nucleotide sequence encoding a particular polypeptide, and the term typically refers to genomic DNA of a plant or mRNA generated using the genomic DNA as a template.

In one or more embodiments, when the expression of DREB2A gene is promoted, the DREB2A gene expression level is increased to a significant extent, compared with a plant to which allantoin is not applied. Whether or not the expression of DREB2A gene is promoted in a plant can be inspected by detecting an increase in the level of mRNA encoding the DREB2A polypeptide and/or an increase in the level of the DREB2A polypeptide in a plant. An extent of promotion of the DREB2A gene expression is not particularly limited. When the DREB2A gene expression level in a plant, to which the DREB2A gene expression promoting agent is not applied, is defined as 100, the DREB2A gene expression level is, for example, about 120 or higher, about 150 or higher, or about 200 or higher in a plant to which the DREB2A gene expression promoting agent is applied. The DREB2A gene expression level may also be, for example, about 400 or lower, about 300 or lower, or about 200 or lower in a plant to which the DREB2A gene expression promoting agent is applied.

In one or more embodiments, when the expression of HSF3 gene is suppressed, the HSF3 gene expression level is decreased to a significant extent, compared with a plant to which allantoin is not applied. Whether or not the expression of HSF3 gene is suppressed in a plant can be inspected by detecting a decrease in the level of mRNA encoding the HSF3 polypeptide and/or a decrease in the level of the HSF3 polypeptide in a plant. An extent of suppression of the HSF3 gene expression is not particularly limited. When the HSF3 gene expression level in a plant, to which the DREB2A gene expression promoting agent is not applied, is defined as 100, the HSF3 gene expression level is, for example, about 90 or lower, about 80 or lower, or about 75 or lower in a plant to which the DREB2A gene expression promoting agent of the present invention is applied.

The method may be applied to any plants in need of promotion of the expression of DREB2A gene. Examples thereof include plants that are cultivated in the environment in which plants may be exposed to high temperature stress, such as the temperature conditions as described above, and other stress. Specific plant species are described above.

In one or more embodiments, the DREB2A gene expression promoting agent contains allantoin and is capable of promoting the expression of DREB2A gene in a plant. The agent may be allantoin itself or a composition comprising allantoin and other components. The DREB2A gene expression promoting agent can contain allantoin in an amount effective for promoting the expression of DREB2A gene in the plant. The DREB2A gene expression promoting agent can also contain allantoin in an amount effective for suppression of the expression of HSF3 gene.

The DREB2A gene expression promoting agent may be in any form, such as a solid or liquid.

In one or more embodiments, when the DREB2A gene expression promoting agent is an allantoin-containing composition, the composition can be the same allantoin-containing composition as the high temperature stress resistance-improving agent described above.

In one or more embodiments, a method of applying the DREB2A gene expression promoting agent to a plant is not particularly limited, and the DREB2A gene expression promoting agent or allantoin released from the DREB2A gene expression promoting agent may be brought into contact with a part of a plant, such as a root, a stem, or a leaf of a plant. The DREB2A gene expression promoting agent may be directly applied to the plant, or the DREB2A gene expression promoting agent may be applied to a cultivation medium, such as soil in which the plant is fixed. In one or more embodiments of the present invention, the DREB2A gene expression promoting agent can be applied to a plant in such a manner that allantoin is applied to the plant in an amount effective for promoting the expression of DREB2A gene in the plant. In one or more embodiments of the present invention, the DREB2A gene expression promoting agent can be applied to a plant in such a manner that allantoin is applied to the plant in an amount effective for suppressing the expression of HSF3 gene in the plant.

In one or more embodiments, although the timing of applying the DREB2A gene expression promoting agent to a plant is not particularly limited, the DREB2A gene expression promoting agent may be applied to the plant before the plant receives stress (e.g., high temperature stress). In one or more embodiments, the DREB2A gene expression promoting agent promotes the expression of DREB2A gene. As described above, the expression of various stress resistant genes may be induced upon the expression of DREB2A gene. Accordingly, a plant, to which the DREB2A gene expression promoting agent is applied before the plant receives stress may achieve stress resistance in advance, and viability thereof upon the plant receives stress may be high.

In one or more embodiments, when the DREB2A gene expression promoting agent is applied to the plant before the plant receives stress, the time point at which the DREB2A gene expression promoting agent is applied to the plant is designated as "T1" and the time point at which exposure of the plant to the stress is initiated is designated as "T2." In such a case, the period from T1 to T2 may be 0.5 to 10 days, 0.5 to 9 days, 0.5 to 8 days, 0.5 to 7 days, 0.5 to 6 days, 0.5 to 5 days, 0.5 to 4 days, 0.5 to 3 days, 0.5 to 2 days, or 0.5 to 1.5 days. In such embodiments, the plant having the stress resistance improved through application of the DREB2A gene expression promoting agent is exposed to the stress. Thus, the viability after the plant is exposed to the stress can be high. The DREB2A gene expression promoting agent may be applied to the plant N times (N is 2 or greater) before the plant receives stress. In such a case, the period from $T1_n$ ($n$ is an integer of 1 to N) at which the DREB2A gene expression promoting agent is applied to T2 may be within the range described above. In one or more embodiments, applying the DREB2A gene expression promoting agent a plurality of times can further improve stress resistance of the plant.

In the present disclosure, the DREB2A gene includes genes comprising a nucleotide sequence encoding a polypeptide annotated as "dehydration-responsive element-binding protein 2A" or "dehydration-responsive element-binding protein 2A-like" in the database provided by the National Center for Biotechnology Information (NCBI) (http://www.ncbi.nlm.nih.gov/) or other databases and genes comprising a nucleotide sequence encoding a polypeptide having a function homologous to the polypeptides described above.

The genes comprising a nucleotide sequence encoding a polypeptide annotated as "dehydration-responsive element-binding protein 2A" or "dehydration-responsive element-binding protein 2A-like" in the database provided by NCBI (http://www.ncbi.nlm.nih.gov/) can be confirmed on the basis of the results of search demonstrated in the website at the URL indicated below: http://www.ncbi.nlm.nih.gov/gene/?term=dehydration-responsive+element-binding+protein+2A.

For example, the nucleotide sequence of cDNA of the DREB2A gene of *Arabidopsis thaliana* (AGI code: AT5G05410) is shown in SEQ ID NO: 1. A partial nucleotide sequence at positions 189 to 1196 in the nucleotide sequence of SEQ ID NO: 1 is a region encoding the DREB2A polypeptide.

In one or more embodiments, expression of a gene comprising a nucleotide sequence encoding a polypeptide having functions homologous to a polypeptide annotated as "dehydration-responsive element-binding protein 2A" or "dehydration-responsive element-binding protein 2A-like" may be promoted in some target plants.

Examples of genes comprising a nucleotide sequence encoding a polypeptide having a function homologous to the polypeptides annotated as dehydration-responsive element-binding protein 2A or dehydration-responsive element-binding protein 2A-like include, but are not limited to:

(1) a gene comprising a nucleotide sequence encoding a polypeptide comprising an amino acid sequence derived from the amino acid sequence of the DREB2A polypeptide of *Arabidopsis thaliana* encoded by a partial nucleotide sequence at positions 189 to 1196 in the nucleotide sequence of SEQ ID NO: 1 by substitution, deletion, insertion, and/or addition of one or several, such as 1 to 20, 1 to 15, 1 to 10, 1 to 5, 1 to 3, or 1 or 2 amino acids and the polypeptide having a function homologous to the DREB2A polypeptide of *Arabidopsis thaliana*; and (2) a gene comprising a nucleotide sequence encoding a polypeptide comprising an amino acid sequence having sequence identity of about 60% or higher, about 70% or higher, about 80% or higher, about 85% or higher, about 90% or higher, about 95% or higher, or about 98% or higher to the amino acid sequence of the DREB2A polypeptide of *Arabidopsis thaliana* and the polypeptide having a function equivalent to the DREB2A polypeptide of *Arabidopsis thaliana*.

In the present disclosure, amino acid sequence identity can be determined by, for example, techniques or sequence analysis software well known in the art. The term "amino acid sequence identity" refers to the proportion (%) of the number of consistent amino acid residues relative to the total number of amino acid residues (including the number of gaps when gaps are inserted), when, for example, the amino acid sequence of the DREB2A polypeptide of *Arabidopsis thaliana* and another amino acid sequence are aligned by inserting gaps, according to need, so as to maximize the degree of consistency between these two amino acid sequences, and amino acid sequence identity can be determined using protein search systems, such as BLAST or FASTA (Karlin, S. et al., 1993, Proceedings of the National Academic Sciences, U.S.A., Vol. 90, pp. 5873-5877: Altschul, S. F. et al., 1990, Journal of Molecular Biology, Vol. 215, pp. 403-410: Pearson, W. R. et al., 1988, Proceedings of the National Academic Sciences, U.S.A., Vol. 85, pp. 2444-2448).

In the present disclosure, the HSF3 gene includes genes comprising a nucleotide sequence encoding a polypeptide annotated as "heat stress transcription factor A-1b" or "heat stress transcription factor A-1b-like" in the database provided by the National Center for Biotechnology Information (NCBI) (http://www.ncbi.nlm.nih.gov/) or other databases and genes comprising a nucleotide sequence encoding a polypeptide having a function homologous to the polypeptides described above.

The genes comprising a nucleotide sequence encoding a polypeptide annotated as "heat stress transcription factor A-1b" or "heat stress transcription factor A-1b-like" in the database provided by NCBI (http://wwv.ncbi.nlm.nih.gov/) can be confirmed on the basis of the results of search demonstrated in the website at the URL indicated below: http://www.ncbi.nlm.nih.gov/gene/?term=heat+stress+transcription+factor+A-1b.

For example, the nucleotide sequence of cDNA of the HSF3 gene of *Arabidopsis thaliana* (AGI code: AT5G16820) is shown in SEQ ID NO: 2. A partial nucleotide sequence at positions 174 to 1619 in the nucleotide sequence of SEQ ID NO: 2 is a region encoding the HSF3 polypeptide.

In one or more embodiments, expression of a gene comprising a nucleotide sequence encoding a polypeptide having a function homologous to a polypeptide annotated as "heat stress transcription factor A-1b" or "heat stress transcription factor A-1b-like" may be suppressed in some target plants.

Examples of genes comprising a nucleotide sequence encoding a polypeptide having a function homologous to the polypeptides annotated as "heat stress transcription factor A-1b" or "heat stress transcription factor A-1b-like" include, but are not limited to:

(1) a gene comprising a nucleotide sequence encoding a polypeptide comprising an amino acid sequence derived from the amino acid sequence of the HSF3 polypeptide of *Arabidopsis thaliana* encoded by a partial nucleotide sequence at positions 174 to 1619 in the nucleotide sequence of SEQ ID NO: 2 by substitution, deletion, insertion, and/or addition of one or several, such as 1 to 20, 1 to 15, 1 to 10, 1 to 5, 1 to 3, or 1 or 2 amino acids and the polypeptide having a function homologous to the HSF3 polypeptide of *Arabidopsis thaliana*; and (2) a gene comprising a nucleotide sequence encoding a polypeptide comprising an amino acid sequence having sequence identity of about 60% or higher, about 70% or higher, about 80% or higher, about 85% or higher, about 90% or higher, about 95% or higher, or about 98% or higher to the amino acid sequence of the HSF3 polypeptide of *Arabidopsis thaliana* and the polypeptide having a function equivalent to the HSF3 polypeptide of *Arabidopsis thaliana*.

8. Gramineous Plants

In the fields of agriculture and gardening, in which a gramineous plant such as a turf grass or rice is cultivated, the growth of the gramineous plant (which is also referred to as "spindly growth") may be suppressed by growth suppressing agents. A conventional plant growth suppressing agent inhibits the biosynthetic pathway of gibberellin that is a plant hormone, and thereby reducing the amount of gibberellin to suppress the growth of a plant. However, gibberellin is an essential hormone for plant growth, and dwarfing of a turf grass may occur when the gibberellin biosynthesis is inhibited.

One or more embodiments of the present invention suppress the growth of plants such as a plant classified into family Poaceae, and in the present disclosure, such a plant is referred to as a "gramineous plant." Among such gramineous plants, the gramineous plant growth suppressing agent according to one or more embodiments of the present invention effectively suppress the growth of a gramineous plant such as a turf grass or rice (*Oryza sativa*), which may be used in the fields of agriculture and gardening.

The turf grass, which is a target of the growth suppression according to one or more embodiments of the present invention, may be either a warm-season turf grass or a cool-season turf grass. Specific examples of such a turf grass include: warm-season turf grasses, such as plants belonging to family Poaceae, subfamily *Eragrostis*, and plants belonging to family Poaceae, subfamily *Panicum*; and cool-season turf grasses, such as plants belonging to family Poaceae, subfamily *Festuca*. Examples of such plants belonging to family Poaceae, subfamily *Eragrostis* include plants belonging to genus *Cynodon* or genus *Zoysia* Specific plant species thereof include bermudagrass (*Cynodon dactylon*), zoysiagrass (*Zoysia japonica*), and Korean lawn grass (*Zoysia natrella*). Examples of such plants belonging to family Poaceae, subfamily *Panicum* include plants belonging to genus *Stenotaphrum* or genus *Eremochloa*. Specific plant species thereof include saint augustinegrass (*Stenotaphrum secundatum*) and centipede grass (*Eremochloa ophiuroides*). Examples of such plants belonging to family Poaceae, subfamily *Festuca* include plants belonging to genus *Agrostis*, genus *Festuca*, genus *Lolium*, or genus *Poa*. Specific plant species thereof include creeping bentgrass (*Agrosis stolonifera*), tall fescue (*Festuca arundinacea*), creeping red fescue (*Festuca rubra* var. *genuina*), chewing fescue (*Festuca rubra* var. *commutata*), hard fescue (*Festuca ovina* var. *duriuscula*), anual ryegrass (*Lolium multiflorumn*), perennial ryegrass (*Lolium perenne*), and Kentucky bluegrass (*Poa pratensis*).

The gramineous plant used as a target is not limited to a wild-type gramineous plant, and it may be a mutant, a transformant, a genetically-modified plant or crop, or any other type of plants.

Examples of the gramineous plants include gramineous crops and gramineous grasses, such as rice, wheat, barley, rye, oat, millet, sugarcane, corn or maize, sorghum, and turf grass.

In one or more embodiments, one or more gramineous plants mentioned above may be excluded from the target plants.

9. Suppression of the Gramineous Plant Growth

In one or more embodiments, a gramineous plant growth suppressing agent for suppressing the growth of a gramineous plant comprises allantoin as an active ingredient.

In one or more embodiments, a method for suppressing the growth of a gramineous plant comprises a step of applying the above-described gramineous plant growth suppressing agent to a gramineous plant.

One or more embodiments of the present invention are effective for the growth of the plant at a vegetative growth stage, and may be particularly effective for the growth of the plant at a vegetative growth stage after germination.

The gramineous plant growth suppressing agent according to one or more embodiments of the present invention can suppress undesirable growth (spindly growth) of a gramineous plant. For example, when the gramineous plant growth suppressing agent according to one or more embodiments of the present invention is applied to a turf grass, the grass height can be appropriately regulated, and the management of the turf grass can be facilitated by reducing mowing and reducing an amount of waste generated by mowing. When the gramineous plant growth suppressing agent according to one or more embodiments of the present invention is applied to rice, the spindly growth of the rice can be suppressed, and thus, the lodging thereof can be suppressed.

In one or more embodiments, the growth of a gramineous plant may be suppressed, and the plant may have a reduced height, a reduced weight, or a reduced leaf area index (LAI) value, as compared to a control plant such as a gramineous plant to which allantoin is not applied.

For example, the height of the gramineous plant may be reduced by about 10% or more, about 20% or more, about 30% or more, or about 40% or more. The height may also be reduced by about 50% or less, about 40% or less, about 30% or less, or about 20% or less. The weight of the gramineous plant may be reduced by about 10% or more, about 20% or more, about 30% or more, or about 40% or more. The weight may also be reduced by about 50% or less, about 40% or less, about 30% or less, or about 20% or less. The LAI value of the gramineous plant may be reduced by about 10% or more, about 20% or more, about 30% or more, or about 40% or more. The LAI value may also be reduced by about 50% or less, about 40% or less, about 30% or less, or about 20% or less.

The gramineous plant growth suppressing agent according to one or more embodiments of the present invention is not particularly limited. In one or more embodiments, the agent comprises allantoin and has an action to suppress the growth of a gramineous plant. The allantoin used herein may be either allantoin itself, or a composition comprising allantoin and other components in combination.

The gramineous plant growth suppressing agent according to one or more embodiments of the present invention can have any given form such as a solid or a liquid. The solid gramineous plant growth suppressing agent is, for example, a granular composition (granular agent). The liquid gramineous plant growth suppressing agent is, for example, an aqueous solution formulation.

In one or more embodiments, when the gramineous plant growth suppressing agent is an allantoin-containing composition, the composition may further comprise other components useful for the plant, or components necessary for the production of formulations. Such other components include fertilizer components. Such components necessary for the production of formulations include solid carriers, and liquid media such as water or ethanol.

In one or more embodiments, when the gramineous plant growth suppressing agent is an allantoin-containing composition, the production method thereof is not particularly limited. Such an allantoin-containing composition can be produced by mixing individual components, and thereafter, in the case of a solid composition such as a granular composition, by performing operations such as crushing, granulation or drying, as necessary, or in the case of a liquid composition, by performing operations such as stirring or dispersion, as necessary.

In one or more embodiments, the method for suppressing the growth of a gramineous plant comprises a step of applying the above-described gramineous plant growth suppressing agent to a gramineous plant.

The method of applying the gramineous plant growth suppressing agent to a plant is not particularly limited, and in one or more embodiments, the gramineous plant growth suppressing agent, or allantoin released from the gramineous plant growth suppressing agent, is allowed to come into contact with a plant body, such as a root, a stem, a leaf or other parts of the plant. In one or more embodiments, the gramineous plant growth suppressing agent may be applied to such a plant, such that it may be directly contacted with the plant body, or the gramineous plant growth suppressing agent may also be applied to a cultivation medium, such as soil in which the plant body is fixed. In one or more embodiments, a liquid composition or a granular composition comprising allantoin is applied to a gramineous plant, such that it is directly contacted with the plant body thereof or it is contacted with a cultivation medium.

The period, at which the gramineous plant growth suppressing agent according to one or more embodiments of the present invention is applied to a gramineous plant, is not particularly limited. For example, the gramineous plant growth suppressing agent may be applied to a gramineous plant at a vegetative growth stage after germination. For example, the gramineous plant growth suppressing agent may be applied to rice at an initial stage of the vegetative growth stage, such as a seedling stage before tillering. In one or more embodiments, when the gramineous plant growth suppressing agent is applied to a turf grass, which is mowed in suitable time intervals, it can be applied to the turf grass at an initial stage of the vegetative growth stage before initial mowing, or at a suitable time point between mowings.

The dose of the gramineous plant growth suppressing agent according to one or more embodiments of the present invention applied to a gramineous plant is not particularly limited, and the applied dose can be appropriately controlled, depending on various conditions such as plant species and growth stage. In one or more embodiments, with regard to the specific applied dose of the gramineous plant growth suppressing agent, the dose of allantoin applied to a gramineous plant per cultivation area for 1 month may be 0.1 to 13 g/m$^2$/month, 1 to 10 g/m$^2$/month, or 3 to 8 g/m$^2$/month. This applied dose may be used for a turf grass, but it is also effective for rice or other gramineous plants. In one or more embodiments, when the applied dose of allantoin is in the aforementioned range, the growth of a gramineous plant can be significantly suppressed.

In one or more embodiments, the gramineous plant growth suppressing agent may be applied dividedly over several times, and the agent may be applied to a gramineous plant that is at a vegetative growth stage in time intervals. The frequency or number of applications can be determined, depending on the form of the gramineous plant growth suppressing agent. For example, when the gramineous plant growth suppressing agent is an aqueous solution formulation, the agent may be applied dividedly over 2 to 10 times per month, or over 3 or 4 times per month, so that a total of the applied dose of allantoin per month can be in the aforementioned range.

10. Production of Gramineous Plant

One or more embodiments of the present invention relate to a method for producing a gramineous plant, comprising a cultivation step of cultivating the gramineous plant. The cultivation step comprises suppressing the growth of the gramineous plant by a method comprising a step of applying a gramineous plant growth suppressing agent comprising allantoin as an active ingredient to the gramineous plant.

Because this method for producing a gramineous plant can suppress undesired growth of a gramineous plant, it is possible to efficiently produce a gramineous plant of interest by the method according to one or more embodiments of the present invention.

In one or more embodiments, the cultivation step can be carried out according to a general step of cultivating a gramineous plant as a target, and the growth of the gramineous plant is suppressed.

EXAMPLES

Hereafter, one or more embodiments of the present invention are described with reference to examples described below. The technical scope of the present invention is not limited to these examples.

Experiment 1. Evaluation of High Temperature Stress Resistance of *Arabidopsis thaliana* in which Allantoin is Accumulated 1. Plant Material The 3 lines of *Arabidopsis thaliana* L. Heynh., accession Columbia-0 with different genetic backgrounds indicated below were used.
(1) Wild-type line (WT)
(2) Allantoinase gene-deletion line (aln-1)
(3) Allantoinase gene-deletion line complemented with allantoinase gene (aln-1 35S:ALN)

These plants are the same as those used in Watanabe, S. et al., Plant Cell Environ., 37: 1022-1036, 2014. The complemented line of the allantoinase gene-deletion line (aln-1 35S:ALN) is the same as the line indicated as "35Spro:ALN/aln-1" in Watanabe, S. et al., Plant Cell Environ., 37: 1022-1036, 2014.

The allantoinase gene-deletion line of (2) above (SALK_000325, Yang. J. and Han K.-H. Plant Physiology, 134: 1039-1049) was obtained from the *Arabidopsis* Biological Resource Center (Ohio State University).

The complemented line of the allantoinase gene-deletion line of (3) above (aln-1 35S:ALN) was obtained by introducing DNA encoding the full-length sequence of allantoinase derived from the wild-type *Arabidopsis thaliana* line into the aln-1 using a vector. A specific method of preparation thereof is as described in Watanabe, S. et al., Plant Cell Environ., 37: 1022-1036, 2014.

2. Culture Medium

A salt mixture for the half-strength Murashige & Skoog medium (Murashige T., F. Skoog F. 1962, A revised medium for rapid growth and bioassays with tobacco tissue cultures, Physiologia *Plantarum* 15: 473-497), sucrose, vitamins, and gellan gum (solidifier) were dissolved in MES (2-(N-morpholino)ethanesulfonic acid) buffer. The solution was autoclaved, dispensed in amounts of 25 ml each into a deep sterilized petri dish FX (90×20 mm, Sansei Medical Co., Ltd.), and allowed to solidify in the clean bench to obtain ½ MS solid medium. The resulting ½ MS solid medium contains the components at concentrations shown in Table 1.

TABLE 1

| Composition | Final concentration |
| --- | --- |
| Salt mixture for Murashige & Skoog medium (Wako Pure Chemical industries, Ltd.) | 2.3 g/l |
| Sucrose (Wako Pure Chemical Industries, Ltd.) | 10 g/l |
| MS vitamins | ** |
| MES (50 g/l, pH 5.7 with KOH) | 10 ml/l |
| Gellan gum (Wako Pure Chemical Industries, Ltd.) | 4 g/l |

**The final concentration of MS vitamins is as follows: 0.25 mg/l thiamine hydrochloride; 0.25 mg/l nicotinic acid; 0.25 mg/l pyridoxine hydrochloride; 1 mg/l glycine; and 50 mg/l myo-inositol. A stock solution of the composition at a concentration 500 times greater than that was used for preparing the medium.

3. Growth Conditions and High Temperature Stress Treatment (1) Several hundreds of mature seeds of the plant were introduced into a 1.5-ml tube. The treatments (2) to (6) described below were carried out in the clean bench.

(2) 2.5% (v/v) sodium hypochlorite (1 ml) was introduced into the tube containing the seeds, mounted on a small rotation mixer (18 rpm), and sterilized for 10 minutes.

(3) Following spinning-down, the sodium hypochlorite solution was discarded, 1 ml of sterile water was added, and the treatment (2) was carried out.

(4) The treatment (3) was repeated 3 times using sterile water to thoroughly wash the seeds.

(5) A petri dish filled with ½ MS solid medium was radially divided into 3 compartments, and 9 seeds of each line were inoculated into each compartment (27 seeds in total in a petri dish) (FIG. 1A).

(6) The petri dish was introduced into the clean bench while keeping the lid open, water in the vicinity of the seeds was allowed to evaporate (for 20 to 30 minutes), and the petri dish was then sealed with a surgical tape.

(7) Each petri dish was wrapped with aluminum foil and subjected to low-temperature treatment (4° C.) for 2 days for dormancy breaking.

(8) The resultant was transferred to a culture chamber and cultured therein at 22° C. under long-day conditions (light application for 16 hours under fluorescent light: 0.07 mmol photons $m^{-1}$ $s^{-1}$) for 7 days.

(9) The 7-day-old plants aseptically grown in (8) were introduced into an incubator preset to 45° C., and heat shock was applied in the dark for 75, 90, or 105 minutes. A control test was carried out by continuously growing plants at 22° C. without the application of heat shock.

(10) After the heat shock treatment, the petri dish was cooled in an incubator at 22° C. for 10 to 15 minutes, and plants were allowed to grow again under the conditions described in (8) for another 1 week. In case of serious damage, a phenomenon of chlorosis (whitening) of leaves would become observable approximately 3 days after the initiation of the test. The viability was evaluated on the basis of such phenomenon.

The test described above was carried out two times.

4. Results

Figure 1B:
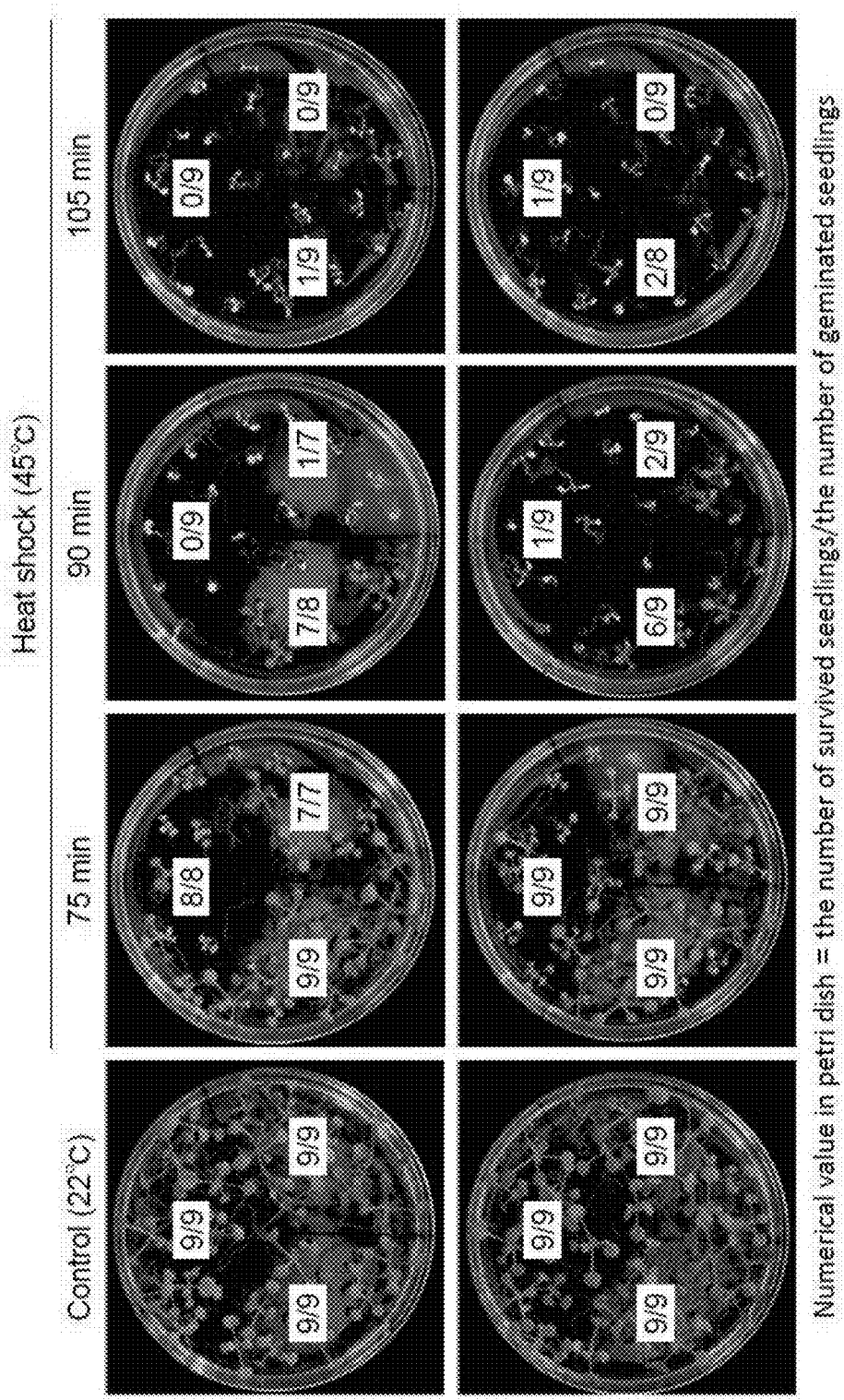
FIG. 1B shows photographs of petri dishes after *Arabidopsis thaliana* has been treated under various heat shock conditions and then grown for 1 week in Experiment 1.

FIG. 1B shows photographs of petri dishes after plants had been treated under various heat shock conditions and grown for 1 week. Plant line positions in each petri dish shown in FIG. 1B are as shown in FIG. 1A. Each numerical value in the petri dish indicates the ratio of "the number of survived seedlings" relative to "the number of geminated seedlings" (the number of survived seedlings/the number of geminated seedlings) in each compartment.

Figure 2:
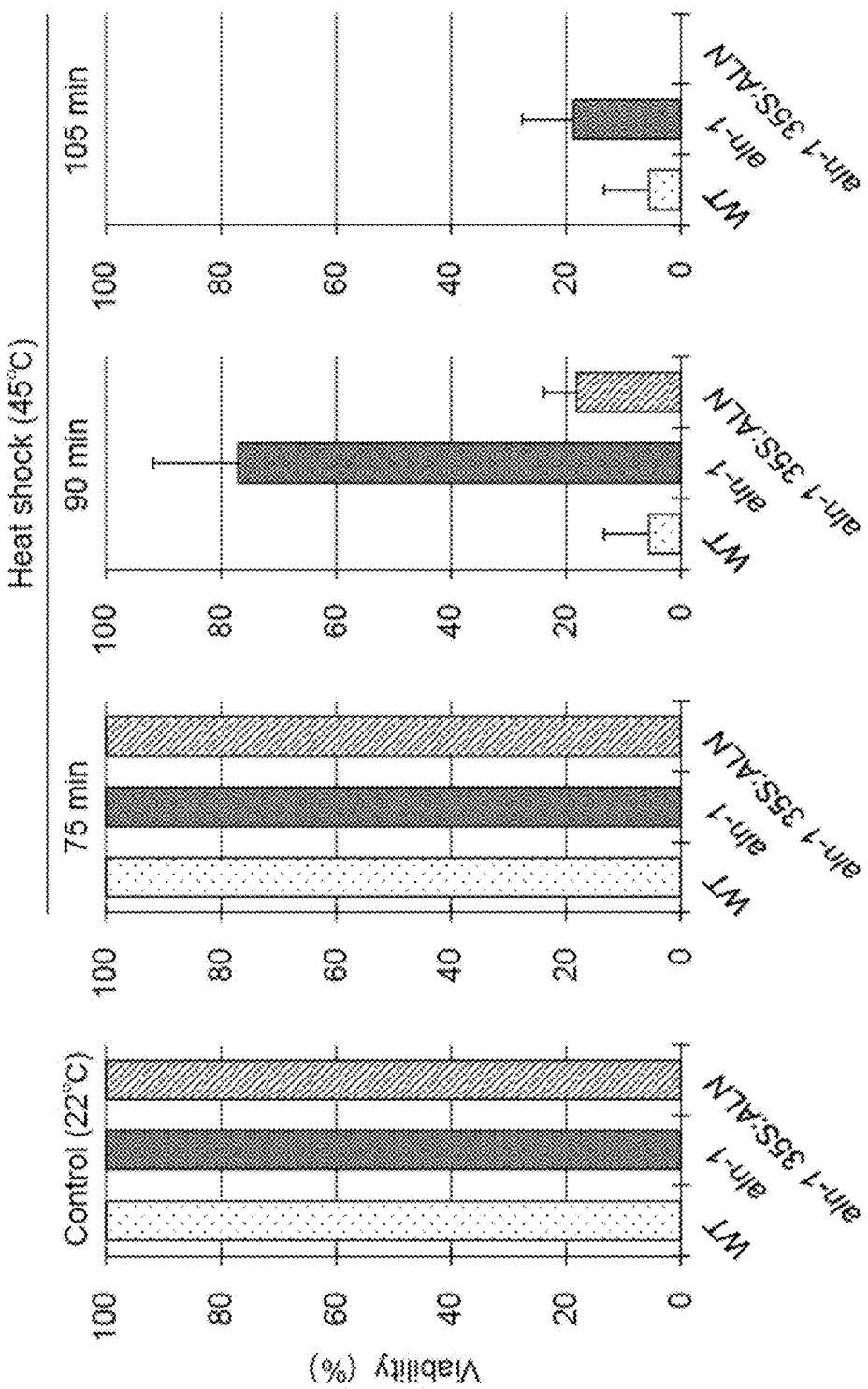
FIG. 2 shows the viability of *Arabidopsis thaliana* treated under various heat shock conditions and then grown for 1 week in Experiment 1.

FIG. 2 shows the viability under various heat shock conditions. The viability shown in FIG. 2 is the value obtained by determining the viability (%) under various conditions based on the number of survived seedlings indicated in FIG. 1B and calculating the average of two tests.

As is apparent from the test results shown in FIG. 1B and FIG. 2, the allantoinase gene-deletion line (aln-1) has resistance to high temperature stress. Since allantoin is not metabolized and is accumulated in the allantoinase gene-deletion line (aln-1), it was concluded that the high temperature stress resistance observed in this experiment was achieved by the presence of allantoin at high concentration in the plant body.

A phenomenon of chlorosis (whitening) of leaves was observed in plants damaged by high temperature stress.

Experiment 2. Provision of High Temperature Stress Resistance to Monocotyledons Via Allantoin Application A 5-cm polypot was mounted on a balance dish BD-2 (AS ONE Corporation), 70 ml of vermiculite (Protoleaf Inc.) was introduced thereinto, 80 ml of culture soil (TAKII & CO., LTD.) was further introduced thereinto, 3 seeds of onion (variety: Neoearth; TAKII & CO., LTD.) were sowed at 3 positions, and 20 ml of vermiculite was further introduced thereinto, so as to cover the soil. Thereafter, 50 ml of tap water was supplied to the balance dish two times. The polypot (together with the balance dish) was mounted on a bat, and the resultant was then introduced into an incubator at 22° C. and 10,000 Lux for a light period of 12 hours and a dark period of 12 hours, so as to initiate cultivation. The day on which cultivation was initiated was designated as Day 0 after sowing. Germination was observed 5 days after sowing. While leaving 3 plants in each pot (i.e., a plant in each position), other plants were removed therefrom 6 days after sowing.

Tap water or an aqueous solution of 1 mM allantoin was applied to each test group (40 ml/pot) 6 days after sowing (hereafter, referred to as the "water treatment group" or the "allantoin treatment group," respectively). Tap water was applied to all the pots (40 ml/pot) 11 days after sowing. The pots mounted on the bats were introduced into the incubator 13 days after sowing (at the 2-true-leaf stage in the case of onions), and the plants were exposed to high temperature stress at 45° C. for 1 hour, 1.5 hours, and 2 hours. Soil in the pots was sufficiently humidified before and after high temperature stress application. After the completion of the high temperature stress treatment, the temperature in the incubator was cooled to 22° C., and cultivation was continued. Water was supplied 2 days after the heat shock treatment (40 ml/pot). Thereafter, water was supplied in an amount of 40 ml per pot at intervals of 2 days.

The viability 3 days after the heat shock treatment was as follows. The viability achieved by the 1-hour treatment of the water treatment group and of the allantoin treatment group was 22.2% and 66.7%, respectively, the viability achieved by the 1.5-hour treatment was 0% and 33.3%, respectively, and the viability achieved by the 2-hour treatment of the water treatment group and of the allantoin treatment group was 0% and 11.1%, respectively. The same viability was observed 8 days after heat shock treatment. Accordingly, the effects of imparting high temperature stress resistance via allantoin application were verified.

The "viability" indicates the proportion of the number of survived plants relative to the number of plants subjected to the heat shock treatment. The viability was calculated by regarding plants that would no longer grow (i.e., the plants with the youngest leaves suffering from physical damage, such as whitening, withering, or curling of leaves) as plants that are not survived.

Figure 3:
FIG. 3 shows photographs of onions 3 days after the initiation of heat shock treatment at 45° C. for 1.5 hours in Experiment 2.
Figure 3:
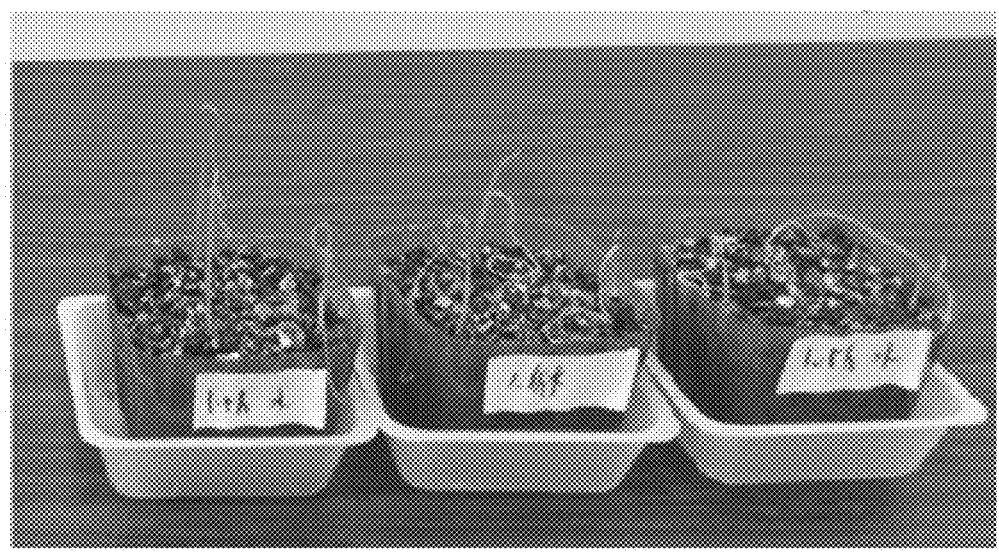

FIG. 3 shows photographs of plants subjected to heat shock treatment at 45° C. for 1.5 hours and then grown for 3 days. In FIG. 3, the upper photograph shows plants of the allantoin treatment group (viability: 33.3%) and the lower photograph shows plants of the water treatment group (viability: 0%).

Experiment 3. Provision of High Temperature Stress Resistance to Dicotyledons Via Allantoin Application A 5-cm polypot was mounted on a balance dish BD-2 (AS ONE Corporation), 70 ml of vermiculite (Protoleaf Inc.) was introduced thereinto, 80 ml of culture soil (TAKII & CO., LTD.) was further introduced thereinto, 3 seeds of *Brassica chinensis* komatsuna (variety: Rakuten, TAKII & CO., LTD.) were sowed at the center of the pot, and 20 ml of vermiculite was further introduced thereinto, so as to cover the soil. Thereafter, 50 ml of tap water was supplied to the balance dish two times. The polypot (together with the balance dish) was mounted on a bat and introduced into an incubator at 22° C. and 10,000 Lux for a light period of 12 hours and a dark period of 12 hours, so as to initiate cultivation. The day on which cultivation was initiated was designated as Day 0 after sowing.

Germination was observed 3 days after sowing. While leaving one plant in each pot, other plants were removed therefrom 6 days after sowing. Tap water or an aqueous solution of 1 mM allantoin was applied to each test group (40 ml/pot) 6 days after sowing. Tap water was applied to all the pots (40 ml/pot) 11 days after sowing. Tap water or an aqueous solution of 1 mM allantoin was applied to each test group (40 ml/pot) 13 days after sowing. The pots mounted on the bats were introduced into the incubator 14 days after sowing (at the 2-true-leaf stage in the case of *Brassica chinensis* komatsuna), and the plants were exposed to high temperature stress at 45° C. for 1 hour. Soil in the pots was sufficiently humidified before and after high temperature stress application. After the completion of the high temperature stress treatment, the temperature in the incubator was cooled to 22° C., and cultivation was continued. Water was supplied 2 days after the heat shock treatment (40 ml/pot). Thereafter, water was supplied in an amount of 40 ml per pot at intervals of 2 days.

The viability 7 days after the heat shock treatment was as follows. The viability achieved by the 1-hour treatment of the water treatment group and of the allantoin treatment group was 33.3% and 100%, respectively. Accordingly, the effects of imparting high temperature stress resistance via allantoin application were verified.

The "viability" indicates the proportion of the number of survived plants relative to the number of plants subjected to the heat shock treatment. The viability was calculated by regarding plants that would no longer grow (i.e., the plants with the youngest leaves suffering from physical damage, such as whitening, withering, or curling of leaves) as plants that are not survived.

Figure 4:
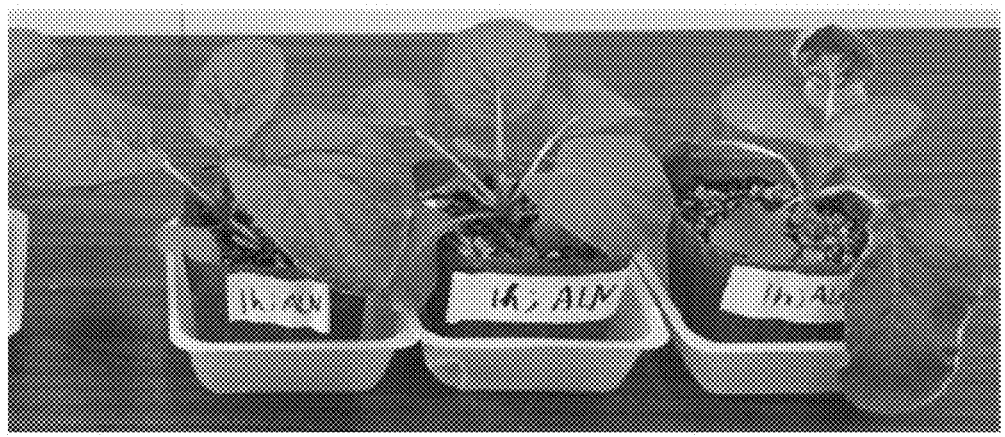
FIG. 4 shows photographs of *Brassica chinensis* komatsuna 7 days after the initiation of heat shock treatment at 45° C. for 1 hour in Experiment 3.
Figure 4:

FIG. 4 shows photographs of plants subjected to heat shock treatment at 45° C. for 1 hours and then grown for 7 days. In FIG. 4, the upper photograph shows plants of the allantoin treatment group (viability: 100%) and the lower photograph shows plants of the water treatment group (viability: 33.3%).

Experiment 4. Promotion of the Expression of DREB2A Gene in Plants in which Allantoin is Accumulated 1. Summary In order to precisely inspect the influence of allantoin imposed on gene expression of *Arabidopsis thaliana* L. Heynh., raw microarray data of the aln-1 mutant that accumulates allantoin as a result of allantoinase gene deletion (NCBI Gene Expression Omnibus accession number GSE44922) was subjected to normalization in accordance with the technique described in Konishi, T., 2004, Three-parameter long normal distribution ubiquitously found in cDNA microarray data and its application to parametric data treatment. BMC Bioinformatics 5: 5. The normalized data was subjected to two-way analysis of variance, the results of analysis were compared with those of wild-type line under strict conditions (P<0.001), and the genes whose transcript levels varied by 3-fold or more were selected (Konishi. T., 2011, Microarray test results should not be compensated for multiplicity of gene contents, BMC Syst. Biol. 5 (Suppl 2): S6). These genes were subjected to gene ontology (GO) biological process analysis using VirtualPlant (version 1.3; http://virtualplant.bio.nyu.edu/cgi-bin/vpweb/).

2. Procedures in Detail

Total RNA was extracted from seedlings of 2-week-old wild-type *Arabidopsis thaliana* line and the aln-1 mutant. Two independent biological samples were used for each genotype. Reverse transcription of RNA into cDNA, labeling thereof, and hybridization thereof to Affymetrics ATH1 Gene Chips were carried out in accordance with the manufacturer's instructions. After the microarrays subjected to hybridization were washed, signals derived from hybridization were collected using the Affymetrics GeneChip Scanner 3000 7G. Thus, raw data from 4 microarrays; i.e., raw data from 2 microarrays of wild-type line and of the aln-1 mutant, were obtained in total. Such procedure is described in Watanabe, S. et al., 2014, Plant Cell Environ., 37: 1022-1036.

Such raw data from microarrays are registered and disclosed under accession numbers of the NCBI Gene Expression Omnibus (http://www.ncbi.nlm.nih.gov/geo/). Such microarray data were normalized by the parametric method using the 3-parameter lognormal distribution model using the SuperNORM service provided by Skylight Biotech, Inc., and the gene expression levels were converted into z-scores (Konishi, T., 2004, as described above). As a result of normalization, gene expression levels between different microarrays can become comparable. The normalized data are registered under Accession Number: GSE73841.

The gene expression levels were compared between wild-type line and the aln-1 mutant. The genes whose expression levels were increased or decreased by at least 3 times in the aln-1 mutant were selected via the two-way analysis of variance (ANOVA) under strict test conditions (P<0.001) in accordance with the method of Konishi, 2011. Using the VirtualPlant (version 1.3; http://virtualplant.bio.nyu.edu/cgi-bin/vpweb/) BioMaps tools with default setting (the Fisher's exact test with false discovery rate correction, P<0.01), gene ontology (GO) biological process analysis was carried out in accordance with the *Arabidopsis* genomic annotation (TAIR release 10; http://*arabidopsis*.org/).

3. Results

As a results of the analysis, the expression level of the DREB2A gene (AGI code: AT5G05410; SEQ ID NO: 1) in the aln-1 mutant line was found to be 3.17 times greater than that in wild-type line.

In contrast, the expression level of the heat shock transcription factor 3 gene (HSF3) (AGI code: AT5G16820, SEQ ID NO: 2) in the aln-1 mutant was found to be 0.577 times greater than that in wild-type line.

Experiment 5. Promotion of the Expression of DREB2A Gene Via Cultivation in Allantoin-Containing Medium Seeds of wild-type *Arabidopsis thaliana* line (Columbia-0) were sterilized in 2.5% (v/v) sodium hypochlorite, sowed in the ½ MS solid medium described in Experiment 1 (Table 1) (the medium was supplemented with 1 mM allantoin; allantoin was not added to the control group: a deep petri dish with a diameter of 90 mm and a height of 20 mm), and then allowed to grow under long-day conditions (in an incubator at 5,000 Lux, a light period of 16 hours and a dark period of 8 hours, 22° C.) for 14 days. Using a commercialized kit, RNA extraction from leaves and stems of *Arabidopsis thaliana* (NucleoSpin RNAII, MACHEREY-NAGEL), reverse transcription (ReverTra Ace qPCR RT Master Mix, TOYOBO), and quantitative PCR (KAPA SYBR FAST qPCR Master Mix, KAPABIOSYSTEMS) were carried out. As a reference gene, ACT2 (AGI code: AT3G18780) was used. As a result, the relative expression level of DREB2A (AGI code: AT5G05410; SEQ ID NO: 1) and that of HSF3 (AGI code: AT5G16820; SEQ ID NO: 2) were 2.2 times and 0.7 times greater than the expression level of the control group, respectively.

Experiment 6. Evaluation of High Temperature Stress Resistance of *Arabidopsis thaliana* Cultivated in Allantoin-Containing Medium 1. Plant Material
The wild-type (WT) line of *Arabidopsis thaliana* (L.) Heynh., accession Columbia-0 described in Experiment 1 was used.

2. Culture Medium
The ½ MS solid medium described in Experiment 1 (Table 1) was used (10 μM, 100 μM, or 1,000 μM allantoin was further added to the allantoin-supplemented group, allantoin was not added to the allantoin-free group, a deep sterilized petri dish No. 903 VALMARK; Ina-Optika Corporation).

Figure 5A:
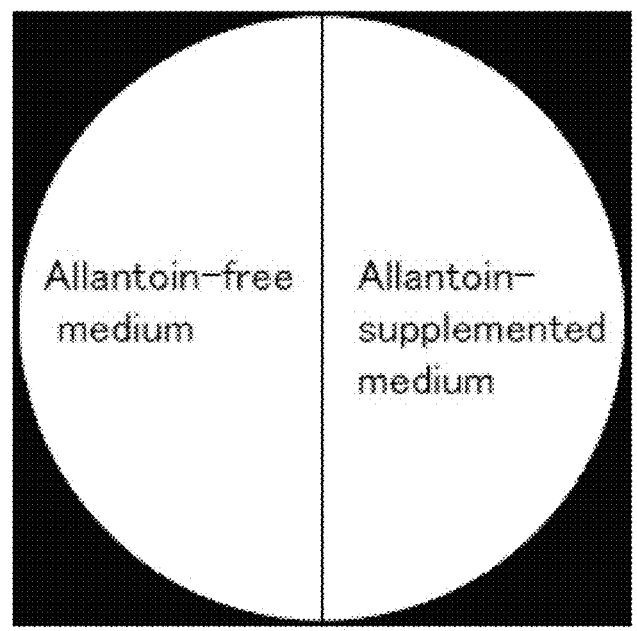
FIG. 5A illustrates compartments in a petri dish used in Experiment 6.

3. Growth Conditions and High Temperature Stress Treatment
(1) Several hundreds of mature seeds of the plant were introduced into a 1.5-ml tube. The treatments (2) to (6) described below were carried out in the clean bench.
(2) 2.5% (v/v) sodium hypochlorite (1 ml) was introduced into the tube containing seeds, mounted on a small rotation mixer (18 rpm), and sterilized for 10 minutes.
(3) Following spinning-down, the sodium hypochlorite solution was discarded, 1 ml of sterile water was added, and the treatment (2) was carried out.
(4) The treatment (3) was repeated 3 times using sterile water to thoroughly wash the seeds.
(5) In the petri dish, a circular accommodation part (a plane view) is divided into 2 semicircular compartments by a partition wall extended toward a diametrical direction. The allantoin-free ½ MS solid medium was accommodated in one of the compartments of the petri dish, the allantoin-supplemented ½ MS solid medium was accommodated in another compartment, and 15 seeds were sowed in each compartment (i.e., 30 seeds in total per petri dish) (FIG. 5A).
(6) The petri dish was introduced into the clean bench while keeping the lid open, water in the vicinity of the seeds was allowed to evaporate (for 20 to 30 minutes), and the petri dish was then sealed with a surgical tape.
(7) Each petri dish was wrapped with aluminum foil and subjected to low-temperature treatment (4° C.) for 2 days for dormancy breaking.
(8) The resultant was transferred to a culture chamber and cultured therein at 22° C. under long-day conditions (light application for 16 hours under fluorescent light: 0.07 mmol photons $m^{-1}$ $s^{-1}$) for 7 days.

(9) The 7-day-old plants aseptically grown in (8) were introduced into an incubator preset to 45° C., and heat shock was applied in the dark for 105 minutes. A control test was carried out by continuously growing plants at 23° C. without the application of heat shock.
(10) Thereafter, the petri dish was cooled in an incubator at 23° C. for 10 to 15 minutes, and the plants were then allowed to grow again for 1 week under the conditions (8). In case of serious damage, a phenomenon of chlorosis (whitening) of leaves would become observable approximately 3 days after the initiation of the test. The viability was evaluated on the basis of such phenomenon.
The test described above was carried out two times.

Figure 5B:
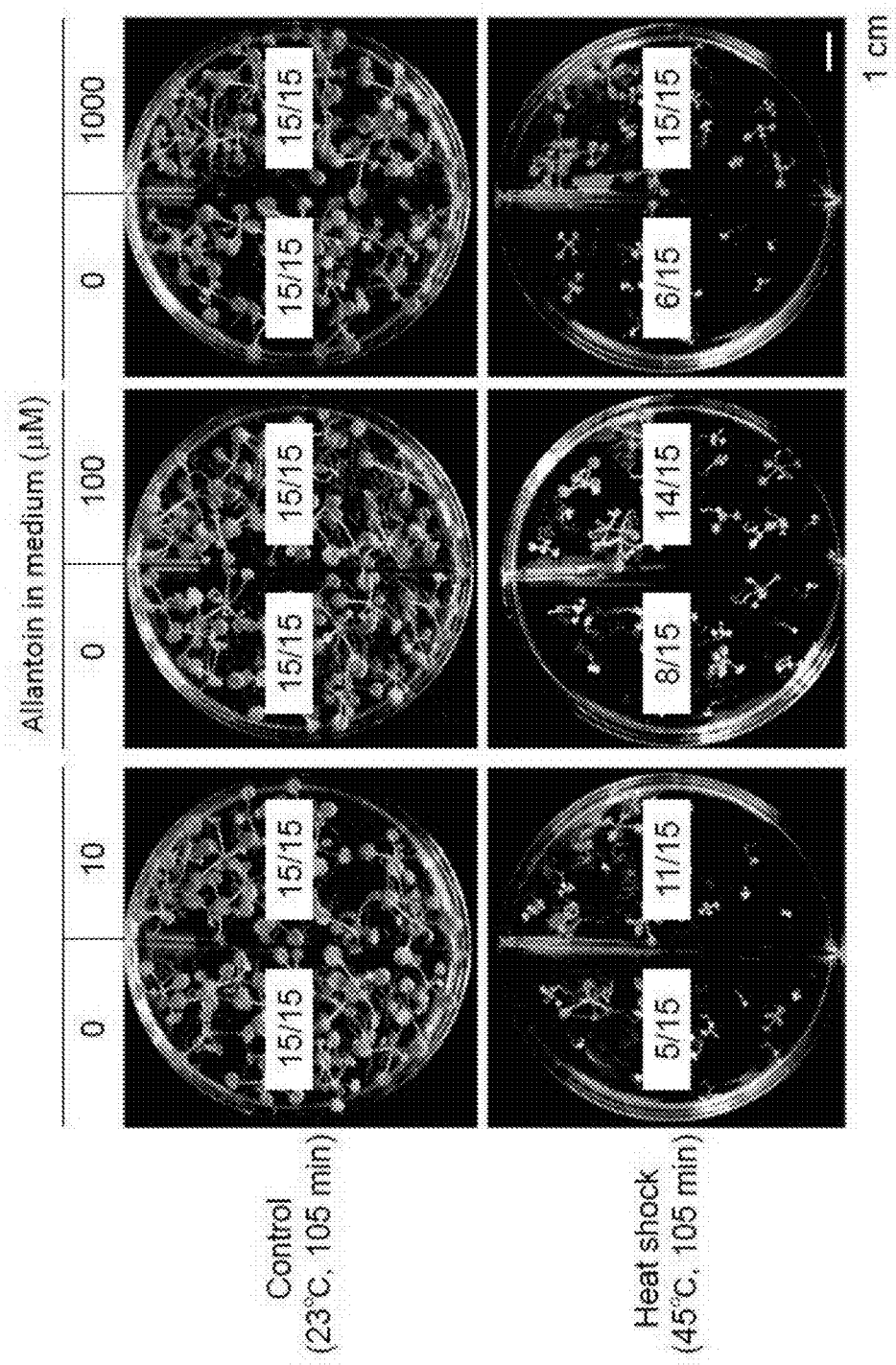
FIG. 5B shows photographs of petri dishes in which *Arabidopsis thaliana* cultivated in media containing allantoin at various concentrations had been treated under heat shock conditions and under control conditions and grown for 1 week in Experiment 6.
Figure 6:
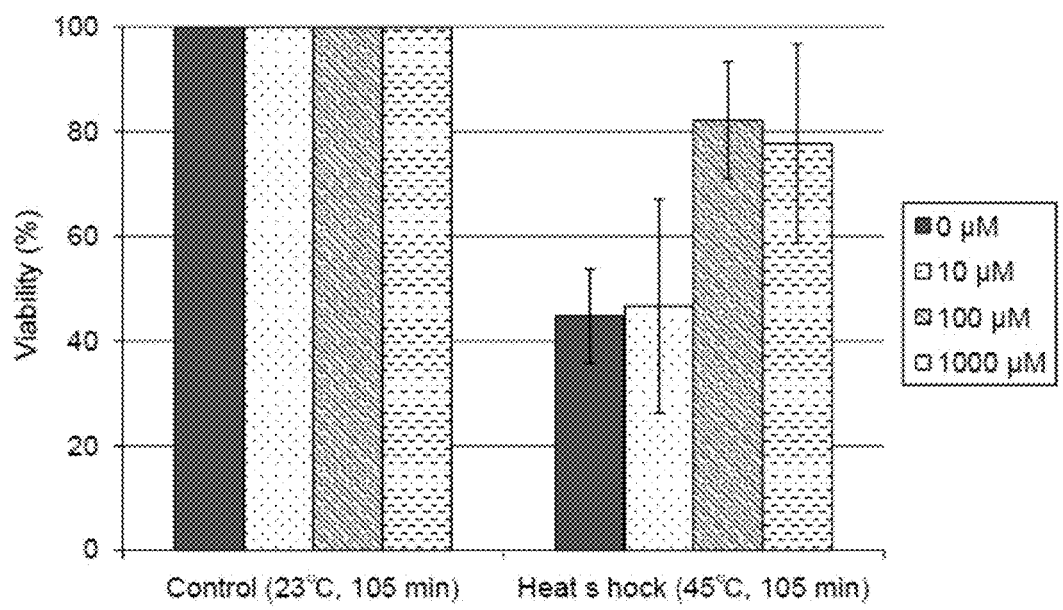
FIG. 6 shows viability of *Arabidopsis thaliana* cultivated in media containing allantoin at various concentrations had been treated under heat shock conditions and under control conditions and grown for 1 week in Experiment 6.

4. Results
FIG. 5B shows photographs of petri dishes after *Arabidopsis thaliana* had been treated under various heat shock conditions and then grown for 1 week. Plant line positions in each petri dish shown in FIG. 5B are as shown in FIG. 5A. Each numerical value in the petri dish indicates the ratio of "the number of survived seedlings" relative to "the number of geminated seedlings" (the number of survived seedlings/ the number of geminated seedlings) in each compartment.
FIG. 6 shows viability under various heat shock conditions. The viability shown in FIG. 6 is the value obtained by determining the viability (%) under various conditions based on the number of survived seedlings indicated in FIG. 5B, determining the viability (%) of another test (not shown), and calculating the average of two tests.
As is apparent from the test results shown in FIG. 5B and FIG. 6, *Arabidopsis thaliana* cultivated in an allantoin-containing medium has resistance to high temperature stress. Since allantoin is accumulated in plant bodies of *Arabidopsis thaliana* cultivated in an allantoin-containing medium, it was concluded that the high temperature stress resistance observed in this experiment was realized by the presence of allantoin at high concentration in plant bodies.
A phenomenon of chlorosis (whitening) of leaves was observed in plants damaged by high temperature stress.

Experiment 7

A polypot with 5 cm each side was placed on a balance dish BD-2 (AS ONE Corporation), and 120 ml of joint- and bed-soil for turf grass (TACHIKAWA HEIWA NOUEN CO., LTD.) was then added into the pot. Thereafter, 140 mg of seeds of creeping bentgrass (variety: 007, Power Shop FUJI) was seeded on the soil, and 3 ml of the soil was further added onto the seeds. Thereafter, 10 ml of tap water was supplied to the balance dish. The polypot (together with the balance dish) was placed on a tray, and was then placed in an artificial climate chamber having a temperature of 20° C., a light intensity of 300 μmol/$m^2$/s, a light period of 16 hours, a dark period of 8 hours, and a humidity of 70%, and thereafter, cultivation was initiated. The day on which cultivation was initiated was defined as Day 0 after sowing. On Day 2 after sowing, 40 ml/pot tap water was applied to all pots. On Day 5 after sowing, germination was confirmed.
On Days 7, 10 and 13 after sowing, tap water (hereinafter referred to as a "water group") or a 1 mM allantoin aqueous solution (hereinafter referred to as an "allantoin group") was applied, in an amount of 40 ml/pot, to individual experiment groups. The experiment was carried out at N=2 in each group. The allantoin used in the present experiment and the subsequent experiments was a racemic mixture.
On Day 13 after sowing, 20 turf grasses were selected from each pot, and the grass height and fresh weight of each grass were then measured. Based on the measured values, a mean value was calculated. The results are shown in Table 2. The grass height was higher and the fresh weight was larger in the water groups than in the allantoin groups.

Figure 7:
FIG. 7 shows a photograph of individual pots on Day 13 after sowing in Experiment 7. Two pots in the lower case of FIG. 7 indicate water groups, whereas two pots in the upper case of FIG. 7 indicate allantoin groups.

FIG. 7 shows a photograph of individual pots on Day 13 after sowing (after three times of applications). Two pots in the lower case of FIG. 7 indicate the water groups, whereas two pots in the lower case of FIG. 7 indicate the allantoin groups. Dwarfing or a reduction in green color caused by application of allantoin was not confirmed.

From the aforementioned results, it could be confirmed that the growth of a turf grass at a vegetative growth stage is suppressed by application of 1 mM allantoin, without undergoing dwarfing or a reduction in green color.

TABLE 2

| Group name | Grass height (cm) | Fresh weight (mg) |
|---|---|---|
| Water | 6.2 | 3.3 |
| Allantoin | 5.6 | 2.9 |

Experiment 8

A polypot with 5 cm each side was placed on a balance dish BD-2 (AS ONE Corporation), and 120 ml of joint- and bed-soil for turf grass (TACHIKAWA HEIWA NOUEN CO., LTD.) was then added into the pot. Thereafter, 140 mg of seeds of creeping bentgrass (variety: 007, Power Shop FUJI) was seeded on the soil, and 3 ml of the soil was further added onto the seeds. Thereafter, 10 ml of tap water was supplied to the balance dish. The polypot (together with the balance dish) was placed on a tray, and was then placed in an artificial climate chamber having a temperature of 20° C., a light intensity of 300 μmol/m$^2$/s, a light period of 16 hours, a dark period of 8 hours, and a humidity of 70%, and thereafter, cultivation was initiated. The day on which cultivation was initiated was defined as Day 0 after sowing. On Day 2 after sowing, 40 ml/pot tap water was applied to all pots. On Day 5 after sowing, germination was confirmed.

On Days 6, 11 and 13 after sowing, tap water (hereinafter referred to as a "water group") or a 0.5 or 1 mM allantoin aqueous solution (hereinafter referred to as an "allantoin group") was applied, in an amount of 40 ml/pot, to individual experiment groups. On and after Day 13 after sowing, a difference was found in the growth of turf glasses among individual groups. On Day 15, 20 turf grasses were selected from each pot, and the grass height and fresh weight of each grass were then measured. Based on the measured values, a mean value was calculated. The results are shown in Table 3.

Figure 8A:
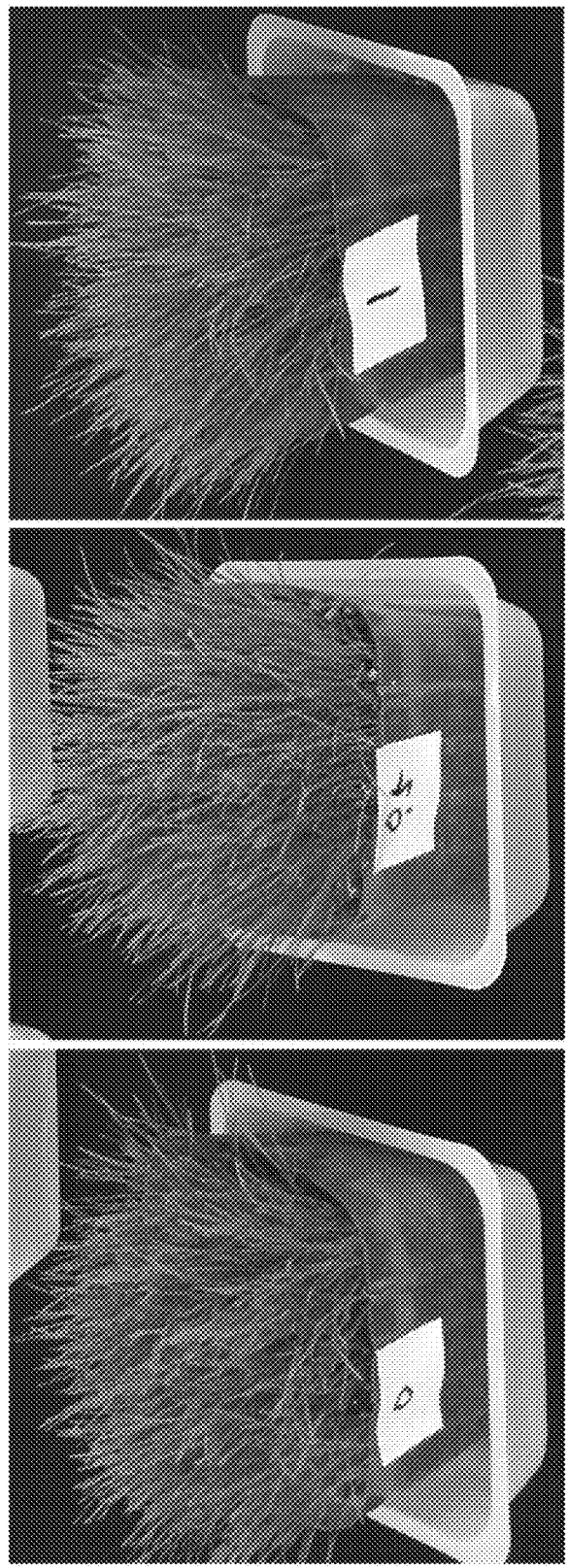
FIG. 8A shows photographs of individual pots on Day 11 after sowing (after two times of applications) in Experiment 8. Regarding the photographs, the left view indicates a water group, the center view indicates a 0.5 mM allantoin group, and the right view indicates a 1 mM allantoin group.
Figure 8B:
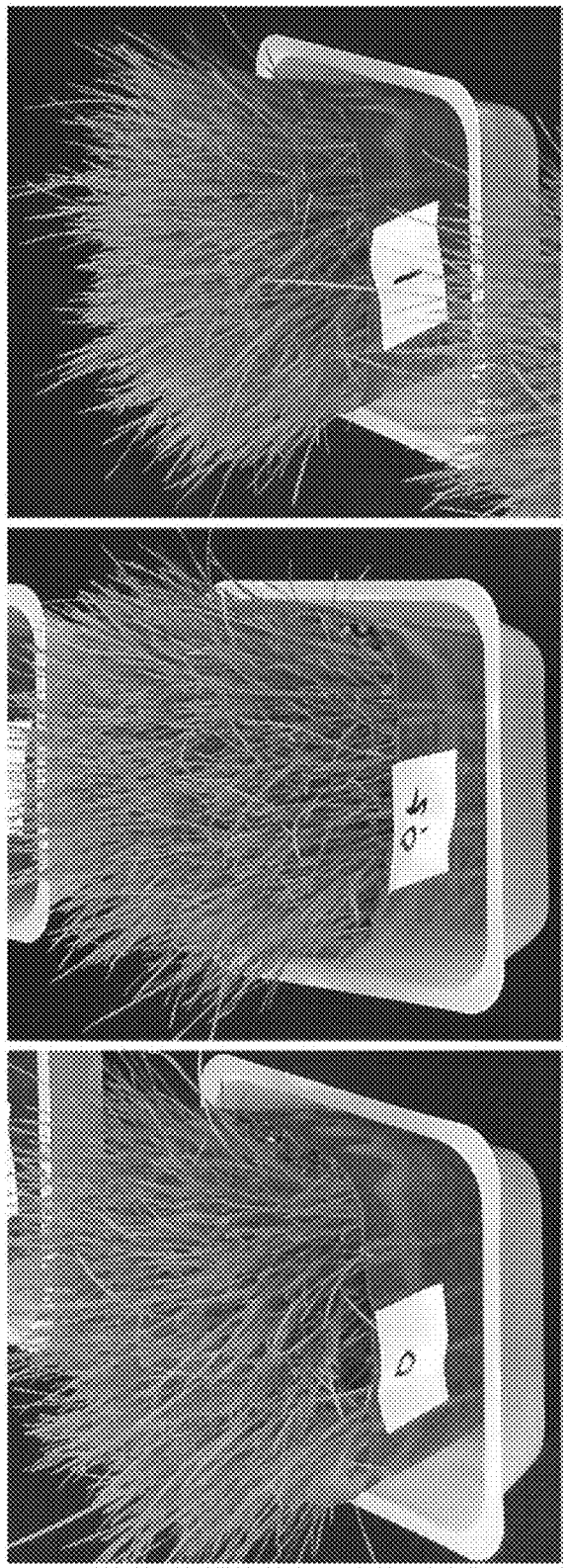
FIG. 8B shows photographs of individual pots on Day 13 after sowing (after three times of applications) in Experiment 8. The configuration of the photographs is the same as that in FIG. 8A.
Figure 8C:
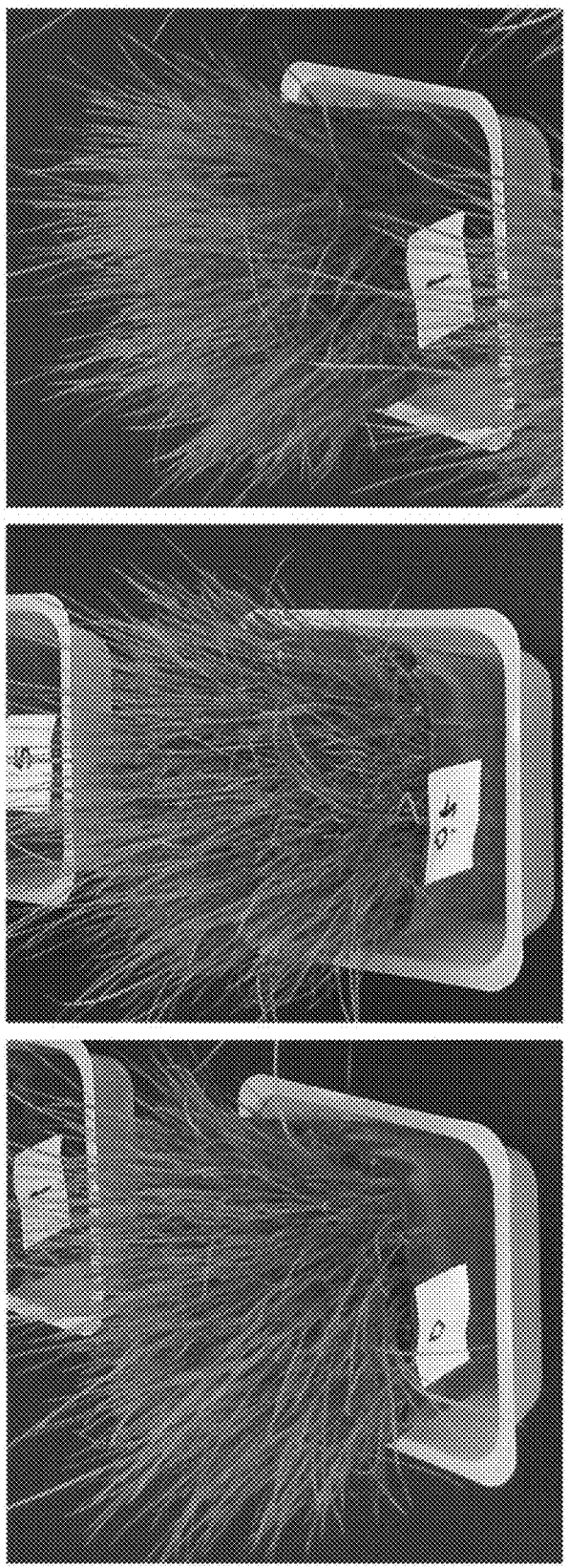
FIG. 8C shows photographs of individual pots on Day 15 after sowing (2 days after the three times of applications) in Experiment 8. The configuration of the photographs is the same as that in FIG. 8A.

FIG. 8A shows photographs of individual pots on Day 11 after sowing (after two times of applications), FIG. 8B shows photographs of individual pots on Day 13 after sowing (after three times of applications), and FIG. 8C shows photographs of individual pots on Day 15 after sowing (2 days after the three times of applications). In the photographs of FIG. 8A to 8C, the left view indicates a water group, the center view indicates a 0.5 mM allantoin group, and the right view indicates a 1 mM allantoin group. Dwarfing or a reduction in green color caused by application of allantoin was not confirmed.

From the aforementioned results, it could be confirmed that the growth of a turf grass at a vegetative growth stage is suppressed by application of 0.5 mM or 1 mM allantoin, without undergoing dwarfing or a reduction in green color.

A total of the applied dose of allantoin per unit area of bentgrass, which was applied for three times of applications in Experiment 8, was 3.8 g/m$^2$ (1.34 g/m$^2$ relative to allantoin nitrogen) in the 0.5 mM allantoin group, whereas it was 7.6 g/m$^2$ (2.69 g/m$^2$ relative to allantoin nitrogen) in the 1 mM allantoin group.

TABLE 3

| Group name | Grass height (cm) | Fresh weight (mg) |
|---|---|---|
| Water | 7.2 | 3.8 |
| 0.5 mM Allantoin | 5.8 | 3 |
| 1 mM Allantoin | 5.9 | 3.1 |

Experiment 9

A 1 mM allantoin aqueous solution or water was applied in an amount of 3 L each to the seedlings of rice (Koshihikari) on Day 26 after sowing (the size of a nursery box: 280×580×28 (mm) (depth×width×height)). A total of the applied dose of allantoin per unit area, which was applied for a single application in Experiment 9, was 3.0 g/m$^2$ (1.05 g/m$^2$ relative to allantoin nitrogen) in the 1 mM allantoin group.

Twelve hours after the application, the seedlings were planted in a paddy field, and were then allowed to grow for 55 days and for 63 days. Thereafter, using a leaf area measurement apparatus LAI-2200 (MEIWAFOSIS CO., LTD.), Leaf Area Index (LAI) which indicates the leaf area under conditions in which the plant still grows in the field, was non-destructively measured. LAI was obtained from two plant bodies in each of the allantoin group and the water group (n=2).

The LAI values of the allantoin group were 1.94 (unit: m$^2$/m$^2$) and 2.04 (m$^2$/m$^2$) on the 55th day, and 2.71 (m$^2$/m$^2$) and 2.82 (m$^2$/m$^2$) on the 63rd day. On the other hand, the LAI values of the water group were 2.63 (m$^2$/m$^2$) and 2.70 (m$^2$/m$^2$) on the 55th day, and 3.12 (m$^2$/m$^2$) and 3.01 (m$^2$/m$^2$) on the 63rd day.

The LAI of the allantoin group was approximately 25% smaller on the 55th day, and approximately 10% smaller on the 63rd day, than the LAI of the water group. This result shows that, when allantoin is applied to rice, the leaf area of the rice is suppressed, namely, the growth of the rice is suppressed at a vegetative growth stage.

All publications, patents, and patent applications cited herein are incorporated herein by reference in their entirety.

In the present disclosure, lower and upper limits may be used alone or may be combined to define a numerical range of values. A specific value described in the present disclosure, which overlaps with a certain numerical range, may be used as a lower limit or an upper limit of the range. Specific compounds, components, or examples listed in the present disclosure may be used alone or in combination with other compounds, components, or examples.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A method for cultivating a plant, comprising:
applying allantoin to a plant;
exposing the plant to a temperature of about 30° C. or more for at least about 60 minutes; and
growing the plant in a cultivation medium.

2. The method according to claim 1, wherein exposing the plant to the temperature is performed at a temperature of about 45° C. or more for at least about 90 minutes.

3. The method according to claim 1, wherein 0.1 to 13 g/m²/month of the allantoin is applied to the plant.

4. The method according to claim 1, wherein the cultivation medium is soil.

5. The method according to claim 1, wherein the plant is converted to a high temperature stress resistant plant after exposing the plant to the temperature.

6. The method according to claim 5, wherein the high temperature stress resistant plant has an increased DREB2A expression level of about 1.2-fold or more, as compared to a DREB2A expression level in a plant grown without allantoin.

7. The method according to claim 6, wherein the high temperature stress resistant plant has an increased HSF3 expression level of about 0.9-fold or less, as compared to an HSF3 expression level in the plant grown without allantoin.

8. The method according to claim 5, wherein the high temperature stress resistant plant is resistant to whitening, withering, or curling of plant leaves.

9. The method according to claim 5, wherein the plant is a gramineous plant at a vegetative growth phase, and wherein spindly growth of the plant is suppressed after applying the allantoin to the plant.

10. The method according to claim 9, wherein the gramineous plant is a turfgrass plant.

11. The method according to claim 9, wherein the gramineous plant is a rice plant.

12. The method according to claim 9, wherein the gramineous plant is grown for at least 26 days from seeding.

13. The method according to claim 9, wherein the gramineous plant after growing the plant has a height, a weight, or a leaf area index (LAI) value that is reduced by about 10% or more, as compared to a height, a weight, or an LAI value of a gramineous plant grown without allantoin.

14. The method according to claim 1, further comprising applying to the plant a pesticide selected from the group consisting of a herbicide, a germicide, a fungicide, an insecticide, and a pest attractant substance.

15. The method according to claim 1, wherein exposing the plant to the temperature is performed 0.5 to 10 days after applying the allantoin to the plant.

16. The method according to claim 1, further comprising adding a fertilizer component to the cultivation medium, wherein the fertilizer component is selected from the group consisting of ammonium sulfate, ammonium nitrate, ammonium chloride, urea, lime nitrogen, ammonium phosphate, potassium phosphate, superphosphate, triple superphosphate, fused phosphate fertilizer, multi-phosphate fertilizer, phosphorous acid, potassium sulfate, potassium chloride, and potassium bicarbonate.

17. The method according to claim 1, wherein applying the allantoin to the plant is performed by irrigating the cultivation medium with a liquid formulation, wherein the liquid formulation comprises the allantoin at a concentration of about 10 to 5,000 ppm.

18. The method according to claim 17, further comprising, prior to applying the allantoin to the plant, preparing the liquid formulation by dissolving a solid formulation in water or an aqueous solution, wherein the solid formulation comprises:
    at least 60% by weight of the allantoin,
    a total nitrogen content of the composition is about 15% by weight or more,
    a water soluble phosphorus content of the composition is about 5% by weight or more, and
    a water soluble potassium content of the composition is 8% by weight or more.

19. The method according to claim 1, wherein applying the allantoin to the plant is performed by applying a liquid formulation onto the plant via foliar application, wherein the liquid formulation comprises the allantoin at a concentration of about 10 to 5,000 ppm.

20. The method according to claim 19, further comprising, prior to applying the allantoin to the plant, preparing the liquid formulation by dissolving a solid formulation in water or an aqueous solution, wherein the solid formulation comprises:
    at least 60% by weight of the allantoin,
    a total nitrogen content of the composition is about 15% by weight or more,
    a water soluble phosphorus content of the composition is about 5% by weight or more, and
    a water soluble potassium content of the composition is 8% by weight or more.

* * * * *

SEQUENCE LISTING

<160> NUMBER OF SEQ ID NOS: 2

<210> SEQ ID NO 1
<211> LENGTH: 1450
<212> TYPE: DNA
<213> ORGANISM: Arabidopsis thaliana
<220> FEATURE:
<223> OTHER INFORMATION: ecotype: Columbia

<400> SEQUENCE: 1

```
agatattttg atttctgcta aagctgtctg ataaaaagaa gaggaaaact cgaaaaagct     60
acacacaaga agaagaagaa aagatacgag caagaagact aaacacgaaa gcgatttatc    120
aactcgaagg aagagacttt gattttcaaa tttcgtcccc tatagattgt gttgtttctg    180
ggaaggagat ggcagtttat gatcagagtg gagatagaaa cagaacacaa attgatacat    240
cgaggaaaag gaaatctaga agtagaggtg acggtactac tgtggctgag agattaaaga    300
gatgaaagaa gtataacgag accgtagaag aagtttctac caagaagagg aaagtacctg    360
cgaaagggtc gaagaagggt tgtatgaaag gtaaggagga accagagaat agccgatgta    420
gtttcagagg agttaggcaa aggatttggg gtaaatgggt tgctgagatc agagagccta    480
atcgaggtag caggctttgg cttggtactt tccctactgc tcaagaagct gcttctgctt    540
atgatgaggc tgctaaagct atgtatggtc ctttggctcg tcttaatttc cctcggtctg    600
atgcgtctga ggttacgagt acctcaagtc agtctgaggt gtgtactgtt gagactcctg    660
gttgtgttca tgtgaaaaca gaggatccag attgtgaatc taaacccttc tccggtggag    720
tggagccgat gtattgtctg gagaatggtg cggaagagat gaagagaggt gttaaagcgg    780
ataagcattg gctgagcgag tttgaacata actattggag tgatattctg aaagagaaag    840
agaaacagaa ggagcaaggg attgtagaaa cctgtcagca acaacagcag gattcgctat    900
ctgttgcaga ctatggttgg cccaatgatg tggatcagag tcacttggat tcttcagaca    960
tgtttgatgt cgatgagctt ctacgtgacc taaatggcga cgatgtgttt gcaggcttaa   1020
atcaggaccg gtacccgggg aacagtgttg ccaacggttc atacaggccc gagagtcaac   1080
aaagtggttt tgatccgcta caaagcctca actacggaat acctccgttt cagctcgagg   1140
gaaaggatgg taatggattc ttcgacgact tgagttactt ggatctggag aactaaacaa   1200
aacaatatga agcttttttgg atttgatatt tgccttaatc ccacaacgac tgttgattct   1260
ctatccgagt tttagtgata tagagaacta cagaacacgt tttttcttgt tataaaggtg   1320
aactgtatat atcgaaacag tgatatgaca atagagaaga caactatagt ttgttagtct   1380
gcttctctta agttgttctt tagatatgtt ttatgttttg taacaacagg aatgaataat   1440
acacacttgt                                                          1450
```

<210> SEQ ID NO 2
<211> LENGTH: 1833
<212> TYPE: DNA
<213> ORGANISM: Arabidopsis thaliana
<220> FEATURE:
<223> OTHER INFORMATION: ecotype: Columbia

<400> SEQUENCE: 2

```
atgcctgctt tcttcagct ttaagggaaa agatcaaaga ttgggtcttc aacacttgag      60
agagtctctg tctctgtaaa agatatttga gcttgagaag aacagaagaa acttccagga    120
tcaatcaatc gatcaacttt agtgaactaa ctccttgattt ttcattcgaa gttatggaat   180
cggttcccga atccgtacca tcgccgaact cgaatacacc gtcaatacca ccgccggtga   240
```

```
actccgtacc gcctttcttg agtaaaacct acgacatggt tgatgatccg ttgaccaatg    300
aggtcgtttc gtggagcagc gggaacaaca gcttcgtcgt ctggagtgcc ccggagttct    360
cgaaggtgct cttgcccaag tatttcaagc acaacaactt ctccagcttc gtcagacagt    420
taaatactta tggtttcaga aaagttgatc ctgaccgatg ggaatttgca aatgaaggat    480
ttcttagagg ccgaaaacaa ctactgaaga gtattgtcag gagaaaacct tcgcatgtgc    540
agcagaatca gcaacaaact caagttcaga gctcatctgt tggtgcttgt gtcgaggtgg    600
ggaagtttgg aatagaagaa gaagtggaaa gacttaagcg ggataagaat gttcttatgc    660
aagaactcgt caggttaagg cagcaacagc aagctactga aaaccaactg cagaatgtgg    720
gacagaaagt tcaggtgatg gagcaaaggc aacaacaaat gatgtcgttt ttagcaaagg    780
ctgttcaaag tccaggtttc ttaaaccagt tagtacaaca gaataataat gatggcaaca    840
gacaaattcc aggaagcaac aaaaagagga gacttcctgt agatgagcag gagaatcgtg    900
gtgacaatgt ggctaatggt cttaaccgcc agattgttag atatcagccg tcgataaacg    960
aagcagcaca aaatatgctt cgacagttct taaatactag tacctcacct cggtatgaat   1020
cagtttcaaa caatcctgac agtttcctat tgggtgatgt tcccagttct acctctgtag   1080
acaatgggaa cccttcaagt agagtttctg gagtaacatt ggccgagttt tcacccaaca   1140
cagttcagtc agcaacgaat caagtacccg aagcaagttt ggctcatcat cctcaagctg   1200
gtctggttca gccaaatata ggtcaaagtc cggctcaagg agcagcacct gcagactctt   1260
ggagccctga atttgattta gttggatgcg agacagatag tggagagtgt tttgatccaa   1320
taatggctgt tttagatgag tcagaaggcg atgcaatttc tcctgaaggt gagggcaaga   1380
tgaatgagtt actggaggga gtccctaagc tgcccggaat ccaagatcca ttctgggaac   1440
agttcttttc tgttgaactc ccagcgattg cagatacaga cgatattcta tcaggatcag   1500
tggagaataa tgacttggta ttggaacaag aaccaaacga gtggacccgt aatgaacaac   1560
aaatgaagta tcttactgaa caaatgggac tgctttcctc agaagcacag aggaaataaa   1620
gattttcagg ggaggttgca aaaggagata tgaaggaacg aggaatatat cagatggtgt   1680
gtataccctt tacattttta cttaaatgaa aaaaaaacag agagaagaaa cataaaagat   1740
ttaccaccaa gcttgtgaat agttagtaga gatcggtttt tgtgttgttt atattatact   1800
tttgtgtgaa aacgttcatc ttgttcaatt atc                                1833
```